US006677306B1

(12) United States Patent
Veis et al.

(10) Patent No.: US 6,677,306 B1
(45) Date of Patent: Jan. 13, 2004

(54) CHONDROGENIC AND OSTEOGENIC INDUCING MOLECULE

(75) Inventors: Arthur Veis, Skokie, IL (US); Denise R. Nebgen, Houston, TX (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 09/744,128

(22) PCT Filed: Jul. 29, 1999

(86) PCT No.: PCT/US99/17342

§ 371 (c)(1),
(2), (4) Date: May 16, 2001

(87) PCT Pub. No.: WO00/06734

PCT Pub. Date: Feb. 10, 2000

Related U.S. Application Data

(60) Provisional application No. 60/094,489, filed on Jul. 29, 1998.

(51) Int. Cl.⁷ .......................... A61K 38/18; C07K 14/51
(52) U.S. Cl. .......................... 514/12; 530/351; 530/399; 536/23.5; 536/23.51
(58) Field of Search ................................. 530/350, 351, 530/399; 514/2, 8, 12; 424/85.1; 536/23.1, 23.5, 23.51

(56) References Cited

U.S. PATENT DOCUMENTS 4,935,497 A    6/1990   Veis et al. ................... 530/840

FOREIGN PATENT DOCUMENTS

| WO | WO 89/04551 | 9/1989 | ............ A61K/6/00 |
| WO | WO 89/08441 | 9/1989 | |
| WO | WO 00/06734 | 2/2000 | ........... C12N/15/12 |

OTHER PUBLICATIONS

Lan et al. Biochem & Biophy Res. Comm. vol. 188, No. 3, pp. 1253–1260.*
Amar et al., *J. Biol. Chem.*, 266:8609–8618 (1991).
Bang et al., *Arch Surg.*, 94:781–789 (1967).
Bessho et al., *J. Oral Maxillofac Surg.*, 48:162–169 (1990).
Bessho et al., *J. Dent. Res.*, 70:171/175 (1991).
Bonass et al., *Biochem. Biophys. Res. Commun.*, 198:755–763 (1994).
Bonass et al., "Rattus Norvegicus leucine–rich amelogenin peptide precursor", Accession No. 07054 (Mar. 17, 1994).
Bonass et al., *Biochim. Biophys. Acta.*, 1219:690–692 (1994).
Deutsh et al., *Connect Tissue Res.*, 32:97–107 (1995).
Edman et al., *Acta. Chemica Scand.*, 4:283–293 (1950).
Fincham et al., *Connect Tissue Res.*, 32:119–124 (1995).
George et al., *J. Biol. Chem.*, 268:12624–12630 (1993).
George et al., *Connect Tissue Res.*, 33:67–72 (1995).
Gibson et al., *Biochemistry*, 31:8384–8388 (1992).
Gibson et al., *Connect Tissue Res.*, 32:109–114 (1995).
Hammarstrom et al., *J. Clin. Periodontol.*, 24:669–677 (1997).
Hammarstrom, *J. Clin. Periodontal*, 24:658–668 (1997).
Iwata et al., *J. Dent. Res.*, 65:12–22 (1993).
Kohno et al., *J. Biol. Chem.*, 259:13668–13673 (1984).
Koskinen et al., *Connect Tissue Res.*, 14:141–158 (1985).
Kulkarni et al., *J. Dent. Res.*, 77:723 (1998)—Abstract 735.
Laemmli, *Nature*, 227:680–685 (1970).
Li et al., *J. Dent. Res.*, 74:1880–1885 (1995).
Lumsden, *Development Suppl.*, 103:155–169 (1988).
Lyons et al., *Development*, 109:833–844 (1990).
MacDougall et al., *J. Bone Mineral Res.*, 13:422–431 (1998).
McConahey et al., *Int. Arch Allergy*, 29:185–189 (1966).
Nebgen et al., *J. Dent. Res.*, 78:1484–1494 (1999).
Salido et al., *Am. J. Hum. Genet.*, 50:303–316 (1992).
Sawada et al., *Arch Oral Biol.*, 40:1029–1038 (1995).
Simmer et al., *Connective Tissue Res.*, 32:131–136 (1995).
Slavkin et al., *J. Dent. Res.*, 53:157 (1975)–Abstract 409.
Slavkin et al., *Biochem. Biophys. Acta.*, 991:12–18 (1989).
Somerman et al., *J. Dent. Res.*, 66:1551–1558 (1987).
Urist, *Science*, 150:893–899 (1965).
Urist et al., *Methods Enzymol.*, 146:294–312 (1987).
Urist et al., *J. Dent. Res.* (Suppl. 6), 50:1392–1406 (1971).
Vainio et al., *Cell*, 75:45–58 (1993).
Veis et al., *Connect Tissue Res.*, 23:137–144 (1989).
Veis et al., *Biomaterials*, 11:35–37 (1990).
Wang et al., *Proc. Nat'l. Acad. Sci. USA*, 85:9484–9488 (1988).
Whang et al., *J. Biomed. Materials Res.*, 42:491–499 (1998).
Wozney et al., *Science*, 242:1528–1534 (1988).
Wray et al., *Anal. Biochem.*, 118:197–203 (1981).
C. Gibson et al., *Biochemistry*, vol. 30, No. 4, pp. 1075–1079 (1991).
J. Catalano–Sherman et al., *J. Dent. Res.*, 72, No. 12, pp. 1566–1572 (1993).
W.A. Bonass et al., *Adv. Dent., Res.*, 10(2), pp. 182–183 (1996)—abstract only.
T. Takagi et al., *Biochemical and Biophysical Research Communications*, vol. 121, No. 2, pp. 592–597 (1984).
Y. Nakahori et al., *Genomics*, 9, pp. 264–269 (1991).
A.G. Fincham et al., *Calcif. Tissue Int.*, 45, pp. 243–250 (1989).

\* cited by examiner

*Primary Examiner*—Prema Mertz
(74) *Attorney, Agent, or Firm*—Marshall, Gerstein & Borun LLP

(57) ABSTRACT

The present invention is directed to methods of using and compositions comprising amelogenin peptides capable of inducing chondrogenesis and osteogenesis when implanted in vivo, a chondrogenesis in cultures in vitro. Compositions and methods of enhancing bone and cartilage growth using these peptides are described.

11 Claims, 16 Drawing Sheets

(3 of 16 Drawing Sheet(s) Filed in Color)

GCTTC AGACA GAAAG TCACT GAGCA TACAC TCAAG AACCA TCAAGAA

1<♦>2 signal peptide
ATG GGG ACC TGG ATC TTG CTC CTG GGA GCT TTT
MET GLY THR TRP ILE LEU LEU LEU GLY ALA PHE
GCT
ALA
ATG CCC CTA CCA CCT CAT TTG GCC TGC CTT CTG GCT TTA
MET PRO LEU PRO PRO HIS LEU GLY CYS LEU LEU ALA LEU
2<♦>3
AGC TAT GAG AAG CCT CAT TCT CCT TGC AGC CCT ATC AAC ACT
SER TYR GLU LYS PRO HIS SER PRO CYS SER PRO ILE ASN THR
3<♦>4
GCA TTA GTG CTT ACC CCC ATC TTG TCT TCA TAC AGC ATC ATG AGG
ALA LEU VAL LEU THR PRO ILE LEU SER SER TYR SER ILE MET ARG
4<♦>5
CAG CCG CCC CTG CTG AAG CCC TGG TGG CCT CCT AGC CTG ATA GAA
GLN PRO PRO LEU LEU LYS PRO TRP TRP PRO PRO SER LEU ILE GLU
5<♦>6d
TGG CCA GCG ACA GAC AAG CTT AAG AAG CGG TGG GAT GAT TTA
TRP PRO ALA THR ASP LYS LEU LYS LYS ARG TRP ASP ASP LEU
ATT CAG ATG AGA GAA CAC CCG AAG TGG TGG ATA TTG TTT TTA
ILE GLN MET ARG GLU HIS PRO LYS TRP TRP ILE LEU PHE LEU
GGA ATA CAA CAA CAC AAT TAA TTG GAT TGC CTA TCA CTT AGT
GLY ILE GLN GLN HIS ASN TAA LEU ASP CYS LEU SER LEU SER
AAA TTC AAC TCA AAA TAA AAA GTA TTA TTA GCA AAT ATG
LYS PHE ASN SER LYS TAA LYS VAL LEU LEU ALA ASN MET
TTT TAA AAA AAA
6d<♦>7
GTG GAT TAA AAA
VAL ASP TAA

FIG. 11B

SEQUENCE LISTING

<160> NUMBER OF SEQ ID NOS: 17

<210> SEQ ID NO 1
<211> LENGTH: 222
<212> TYPE: DNA
<213> ORGANISM: Recombinant rat amelogenin

<400> SEQUENCE: 1

```
atgcccctac cacctcatcc tgggagccct ggttatatca acttaagcta tgagaagtca      60
cattctcagg ctatcaatac tgacaggact gcattagtgc ttaccccctt gaagtggtac     120
cagagcatga taaggcagcc gcccctgtcc cccattcttc ctgagctgcc tctggaagct     180
tggccagcga cagacaagac caagcgggaa gaagtggatt aa                        222
```

<210> SEQ ID NO 2
<211> LENGTH: 180
<212> TYPE: DNA
<213> ORGANISM: Recombinant rat amelogenin

<400> SEQUENCE: 2

```
atgcccctac cacctcatcc tgggagccct ggttatatca acttaagcta tgaggtgctt      60
accccttga agtggtacca gagcatgata aggcagccgc ccctgtcccc cattcttcct      120
gagctgcctc tggaagcttg gccagcgaca gacaagacca gcgggaaga agtggattaa      180
```

<210> SEQ ID NO 3
<211> LENGTH: 476
<212> TYPE: DNA
<213> ORGANISM: Artificial sequence
<220> FEATURE:
<223> OTHER INFORMATION: Description of Artificial Sequence: PCR Product

<400> SEQUENCE: 3

```
gcttcagaca gaaagtcact gagcatacac tcaagaacca tcaagaaatg gggacctgga      60
tcttgtttgc ctgcctcctg ggagcagctt ttgctatgcc cctaccacct catcctggga    120
gccctggtta tatcaactta agctatgaga agtcacattc tcaggctatc aatactgaca    180
ggactgcatt agtgcttacc cccttgaagt ggtaccagag catgataagg cagccgcccc    240
tgtccccat tcttcctgag ctgcctctgg aagcttggcc agcgacagac aagaccaagc    300
gggaagaagt ggattaaaaa attcagaaga tgagagaacc gaagtggata ctttggttgt    360
ttttaggaat aactcaagaa cacaatgatt tgtgcctaca atcacttagt aaattctgta    420
actaaaaata gtatcatta gcagataata aatgtttta aaaatcaaaa aaaaaa        476
```

<210> SEQ ID NO 4
<211> LENGTH: 89
<212> TYPE: PRT
<213> ORGANISM: Artificial Sequence
<220> FEATURE:
<223> OTHER INFORMATION: Description of Artificial Sequence: PCR Product

<400> SEQUENCE: 4

```
Met Gly Thr Trp Ile Leu Phe Gly Cys Leu Leu Gly Ala Ala Phe Ala
 1               5                  10                  15

Met Pro Leu Pro Pro His Pro Gly Ser Pro Gly Tyr Ile Asn Leu Ser
                20                  25                  30

Tyr Glu Lys Ser His Ser Gln Ala Ile Asn Thr Asp Arg Thr Ala Leu
            35                  40                  45

Val Leu Thr Pro Leu Lys Trp Tyr Gln Ser Met Ile Arg Gln Pro Pro
        50                  55                  60

Leu Ser Pro Ile Leu Pro Glu Leu Pro Leu Glu Ala Trp Pro Ala Thr
 65                  70                  75                  80

Asp Lys Thr Lys Arg Glu Glu Val Asp
                85
```

<210> SEQ ID NO 5
<211> LENGTH: 59
<212> TYPE: PRT
<213> ORGANISM: Recombinant rat amelogenin

<400> SEQUENCE: 5

```
Met Pro Leu Pro Pro His Pro Gly Ser Pro Gly Tyr Ile Asn Leu Ser
 1               5                  10                  15

Tyr Glu Val Leu Thr Pro Leu Lys Trp Tyr Gln Ser Met Ile Arg Gln
                20                  25                  30

Pro Pro Leu Ser Pro Ile Leu Pro Glu Leu Pro Leu Glu Ala Trp Pro
            35                  40                  45
```

```
Ala Thr Asp Lys Thr Lys Arg Glu Glu Val Asp
     50                  55
```

<210> SEQ ID NO 6
<211> LENGTH: 73
<212> TYPE: PRT
<213> ORGANISM: Recombinant rat amelogenin

<400> SEQUENCE: 6

```
Met Pro Leu Pro Pro His Pro Gly Ser Pro Gly Tyr Ile Asn Leu Ser
  1               5                  10                  15

Tyr Glu Lys Ser His Ser Gln Ala Ile Asn Thr Asp Arg Thr Ala Leu
             20                  25                  30

Val Leu Thr Pro Leu Lys Trp Tyr Gln Ser Met Ile Arg Gln Pro Pro
         35                  40                  45

Leu Ser Pro Ile Leu Pro Glu Leu Pro Leu Ala Trp Pro Ala Thr
     50                  55                  60

Asp Lys Thr Lys Arg Glu Glu Val Asp
 65                  70
```

<210> SEQ ID NO 7
<211> LENGTH: 5
<212> TYPE: PRT
<213> ORGANISM: Recombinant rat amelogenin

<400> SEQUENCE: 7

```
Met Pro Leu Pro Pro
  1               5
```

<210> SEQ ID NO 8
<211> LENGTH: 6
<212> TYPE: PRT
<213> ORGANISM: Recombinant rat amelogenin

<400> SEQUENCE: 8

```
Trp Tyr Gln Ser Met Ile
  1               5
```

<210> SEQ ID NO 9
<211> LENGTH: 6
<212> TYPE: PRT
<213> ORGANISM: Recombinant rat amelogenin

<400> SEQUENCE: 9

```
Trp Tyr Gln Asn Met Leu
  1               5
```

<210> SEQ ID NO 10
<211> LENGTH: 15
<212> TYPE: DNA
<213> ORGANISM: Artificial sequence
<220> FEATURE:
<223> OTHER INFORMATION: Description of Artificial sequence: primer

<400> SEQUENCE: 10
atgcctctac cacct                                                    15

<210> SEQ ID NO 11
<211> LENGTH: 18
<212> TYPE: DNA
<213> ORGANISM: Artificial sequence
<220> FEATURE:
<223> OTHER INFORMATION: Description of Artificial sequence: primer

<400> SEQUENCE: 11
tatcatgctc tggtacca					18

<210> SEQ ID NO 12
<211> LENGTH: 29
<212> TYPE: DNA
<213> ORGANISM: Artificial sequence
<220> FEATURE:
<223> OTHER INFORMATION: Description of Artificial sequence: primer

<400> SEQUENCE: 12
ttcccgaatt ccatgcccct accacctca					29

<210> SEQ ID NO 13
<211> LENGTH: 29
<212> TYPE: DNA
<213> ORGANISM: Artificial sequence
<220> FEATURE:
<223> OTHER INFORMATION: Description of Artificial sequence: primer

<400> SEQUENCE: 13
ggccgctcga gttaatccac ttcttcccg					29

<210> SEQ ID NO 14
<211> LENGTH: 30
<212> TYPE: PRT
<213> ORGANISM: Artificial sequence
<220> FEATURE:
<223> OTHER INFORMATION: Description of Artificial sequence: PCR product

<400> SEQUENCE: 14

Met Pro Leu Pro Pro His Pro Gly His Pro Gly Tyr Ile Asn Phe Ser
 1               5                  10                  15

Tyr Glu Val Leu Thr Pro Leu Lys Trp Tyr Gln Ser Met Ile
            20                  25                  30

<210> SEQ ID NO 15
<211> LENGTH: 44
<212> TYPE: PRT
<213> ORGANISM: Artificial sequence
<220> FEATURE:
<223> OTHER INFORMATION: Description of Artificial sequence: PCR product

<400> SEQUENCE: 15

Met Pro Leu Pro Pro His Pro Gly His Pro Gly Tyr Ile Asn Phe Ser
 1               5                  10                  15

Tyr Glu Lys Ser His Ser Gln Ala Ile Asn Thr Asp Arg Thr Ala Leu
            20                  25                  30

Val Leu Thr Pro Leu Lys Trp Tyr Gln Ser Met Ile
        35                  40

<210> SEQ ID NO 16
<211> LENGTH: 194
<212> TYPE: PRT
<213> ORGANISM: Artificial sequence
<220> FEATURE:
<223> OTHER INFORMATION: Description of Artificial sequence: PCR product

<400> SEQUENCE: 16

Met Pro Leu Pro Pro His Pro Gly Ser Pro Gly Tyr Ile Asn Leu Ser
 1               5                  10                  15

Tyr Glu Lys Ser His Ser Gln Ala Ile Asn Thr Asp Thr Arg Ala Leu
            20                  25                  30

```
Val Leu Thr Pro Leu Lys Trp Tyr Gln Ser Met Ile Arg Gln Pro Tyr
            35                  40                  45

Pro Ser Tyr Gly Tyr Glu Pro Met Gly Gly Trp Leu His His Gln Ile
        50                  55                  60

Ile Pro Val Leu Ser Gln Gln His Pro Pro Ser His Thr Leu Gln Pro
 65                  70                  75                  80

His His His Leu Pro Val Val Pro Ala Gln Gln Pro Val Ala Pro Gln
                85                  90                  95

Gln Pro Met Met Pro Val Pro Gly His His Ser Met Thr Pro Thr Gln
            100                 105                 110

His His Gln Pro Asn Ile Pro Pro Ser Ala Gln Gln Pro Phe Gln Gln
            115                 120                 125

Pro Phe Gln Pro Gln Ala Ile Pro Pro Gln Ser His Gln Pro Met Gln
        130                 135                 140

Pro Gln Ser Pro Leu His Pro Met Gln Pro Leu Ala Pro Gln Pro Pro
145                 150                 155                 160

Leu Pro Pro Leu Phe Ser Met Gln Pro Leu Ser Pro Ile Leu Pro Glu
                165                 170                 175

Leu Pro Leu Glu Ala Trp Pro Ala Thr Asp Lys Thr Lys Arg Glu Glu
            180                 185                 190

Val Asp
```

<210> SEQ ID NO 17
<211> LENGTH: 180
<212> TYPE: PRT
<213> ORGANISM: Artificial sequence
<220> FEATURE:
<223> OTHER INFORMATION: Description of Artificial sequence: PCR product

<400> SEQUENCE: 17

```
Met Pro Leu Pro Pro His Pro Gly Ser Pro Gly Tyr Ile Asn Leu Ser
 1               5                  10                  15

Tyr Glu Val Leu Thr Pro Leu Lys Trp Tyr Gln Ser Met Ile Arg Gln
            20                  25                  30

Pro Tyr Pro Ser Tyr Gly Tyr Glu Pro Met Gly Gly Trp Leu His His
            35                  40                  45

Gln Ile Ile Pro Val Leu Ser Gln Gln His Pro Pro Ser His Thr Leu
     50                  55                  60

Gln Pro His His His Leu Pro Val Val Pro Ala Gln Gln Pro Val Ala
 65                  70                  75                  80

Pro Gln Gln Pro Met Met Pro Val Pro Gly His His Ser Met Thr Pro
                85                  90                  95

Thr Gln His His Gln Pro Asn Ile Pro Pro Ser Ala Gln Gln Pro Phe
            100                 105                 110

Gln Gln Pro Phe Gln Pro Gln Ala Ile Pro Pro Gln Ser His Gln Pro
        115                 120                 125

Met Gln Pro Gln Ser Pro Leu His Pro Met Gln Pro Leu Ala Pro Gln
        130                 135                 140

Pro Pro Leu Pro Pro Leu Phe Ser Met Gln Pro Leu Ser Pro Ile Leu
145                 150                 155                 160

Pro Glu Leu Pro Leu Glu Ala Trp Pro Ala Thr Asp Lys Thr Lys Arg
                165                 170                 175

Glu Glu Val Asp
            180
```

CHONDROGENIC AND OSTEOGENIC INDUCING MOLECULE

This application is based on and claims priority of U.S. provisional application serial No. 60/094,489 filed on Jul. 29, 1998.

This work was supported by NIH/NIDR Grants DE 08525 (AV), DE 01374 (AV) and Institutional Training Grant T32 DE 07201 (DRN).

The present invention relates to polypeptides with in vitro chondrogenic and in vivo osteogenic activity.

BACKGROUND OF THE INVENTION

Proteins capable of inducing bone morphogenesis (BMPs) were first identified from extracts of demineralized bone (Urist, 1965), and shortly thereafter from teeth (Bang and Urist, 1967). The bone-derived osteogenic activity was the subject of extensive isolation and purification efforts, until the human BMPs 2–7 were successfully punified and cloned (Wang et al., 1988; Wozney et al., 1988). The BMPs are members of a larger family of growth factors known as the DVR/TGF-β supergene family (Kingsley, 1994). Although the BMPs were originally studied for their osteogenic inductive capabilities, following their cloning an explosion of developmental research revealed that the BMPs have a variety of regulatory functions throughout development, and at the embryonic level, in the transfer of signals during epithelial-mesenchymal interactions.

Bones and teeth are related tissues in that the bone and dentin matrices are comprised of type I collagen fibers that become mineralized by impregnation with crystals of carbonated calcium hydroxyapatite. It can thus be argued that bone and dentin mineralization follow similar pathways, although they do differ in detail. Most of the extracellular matrix proteins that have been found in bone have also been described in dentin. However, dentin contains several specific proteins that have not yet been found in bone.

Bone normally undergoes constant remodeling, with formation and degradation carried out in parallel. Teeth, once they have reached maturity, grow only with the addition of secondary dentin at a low rate, with little if any, normal resorption. Developmental processes represent another major difference. Membrane bone and the bone from the appendicular skeleton are formed by osteoblasts originating from mesenchymal stem cells. Their differentiation and maturation are governed by numerous cytokines and para- and autocrine factors. The non-membrane bones follow an endochondral model during osteogenesis. In contrast, during tooth development, epithelial cells differentiate into ameloblasts, which secrete the enamel, while ectomesenchymal cells derived from the neural crest differentiate into odontoblasts, which secrete the dentin. These differentiation processes occur through a set of staged reciprocal interactions between the epithelial and mesenchymal cells, leading to the formation of the mature tooth (Lumsden, 1988). Epigenetic signals passed between the cells appear to induce the appropriate cellular morphogenesis events. BMP-4 has been localized within the tooth germ and has been proposed as one of the signals regulating the reciprocal transfer of information (Vainio et al., 1993), although BMP-4 alone cannot completely reproduce these changes, and other signals appear to be necessary.

Bang and Urist (1967) demonstrated that demineralized dentin matrix had the same potential as bone matrix to induce uncommitted mesenchymal cells to differentiate, at ectopic sites in vivo, into cartilage and then bone, following a pathway that resembled endochondral bone formation. In fact, dentin matrix implants were more potent in bone induction than bone matrix implants (Urist & Strates, 1971; Somerman et al., 1987; Veis et al., 1989).

By in situ hybridization, transcripts for BMPs-2 and 4 have been localized to the odontoblast cell layer in mouse embryos (Lyons et al., 1990; Vainio et al., 1993). Dentin matrix probably does contain the expressed BMPs. However, the BMP proteins themselves have not been successfully purified from dentin. Beesho et al. (1990, 1991) isolated proteins with BMP-like activity from rabbit and human dentin, but the $NH_2$-terminal amino acid sequence for the human dentin-derived BMP did not resemble that of the known BMP family. In this laboratory, Amar et al. (1991) described the isolation from rat incisor dentin of a polypeptide exhibiting chondrogenic inducing activity (CIA) in cell culture assays (Koskinen et al. 1985, Veis et al., 1989). The amount of protein recovered from rat teeth was small and the $NH_2$-terminal sequencing data was very limited. Nevertheless, as in the report of Bessho et al. (1991), it was clear that the CIA did not correspond to the known BMPs.

It is an object of the present invention to identify and characterize the dentin matrix protein exhibiting chondrogenic and or osteogenic activity.

SUMMARY OF THE INVENTION

The present invention provide chondrogenic and osteogenic inducing molecules (CIM), also called chondrogenic inducing agents (CIA).

In one aspect, the invention provides a chondrogenic and osteogenic inducing molecule having the nucleotide sequence SEQ ID NO: 16. This polynucleotide corresponds to a splice product of the rat amelogenin gene encoded by rat amelogenin gene exons 2, 3 ,4, 5, 6 and 7.

In a preferred embodiment of this aspect, the invention provides a chondrogenic and osteogenic inducing molecule, also referred to herein as "rA4", that has the nucleotide sequence SEQ ID NO: 1. rA4 corresponds to a specific defined splice product of the rat amelogenin gene encoded by rat amelogenin gene exons 2, 3 ,4, 5, 6d and 7.

In another aspect, the invention provides a chondrogenic and osteogenic inducing molecule that has the nucleotide sequence SEQ ID NO:17. This polynucleotide corresponds to a splice product of the rat amelogenin gene that includes exons 2, 3, 5, 6 and 7 of the rat amelogenin gene.

In a preferred embodiment of this aspect, the invention provides a chondrogenic and osteogenic inducing molecule, also referred to herein as "r(A-4)" that has the nucleotide sequence SEQ ID NO:2. r(A-4) corresponds to a specific defined splice product of the rat amelogenin gene that includes exons 2, 3, 5, 6d and 7 of the rat amelogenin gene.

Another aspect of the present invention is directed to nucleic acid sequences complementary to, or showing sequence similarity to, the DNA sequences identified in SEQ ID NOS: 1, 2, 16 and 17. The present invention is also directed to those sequences which are at least 60%, preferably at least 80%, and most preferably at least 95%, especially 98%, identical thereto.

These molecules have surprisingly been found to be useful to induce differentiation of cells to the osteogenic and chondrogenic phenotypes and may be used in a composite cell construct for bone and cartilage regeneration.

Accordingly, the invention provides a composition and a method for enhancing osteogenic and or chondrogenic generation or growth. The method comprises exposing cells to the chondrogenic/osteogenic polypeptides of the invention.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

A. The activity of Sephacryl S-100 fractions 1 and 2, as compared to positive (bBMP) and negative (PBS/BSA) controls. BMP- Bovine bone BMP, 1 mg/ml, kindly provided Dr. M. Urist. PBS- PBS/0.1% BSA. 1- S-100, Fraction 1, 1 mg/ml. 2—S-100, Fraction 2, 1 mg/ml. Fractions 3–11 were comparable to the negative PBS control.

B. A comparison of the concentration dependence of the activity of the combined S-100 (Fractions 1 & 2) with that of recombinant human BMP-2. Note that the rhBMP-2 was active at the 50–100 ng/ml level, while the S-100 stimulated sulfate incorporation to the same degree but at 100–1000 μg/ml levels.

Figure 1:
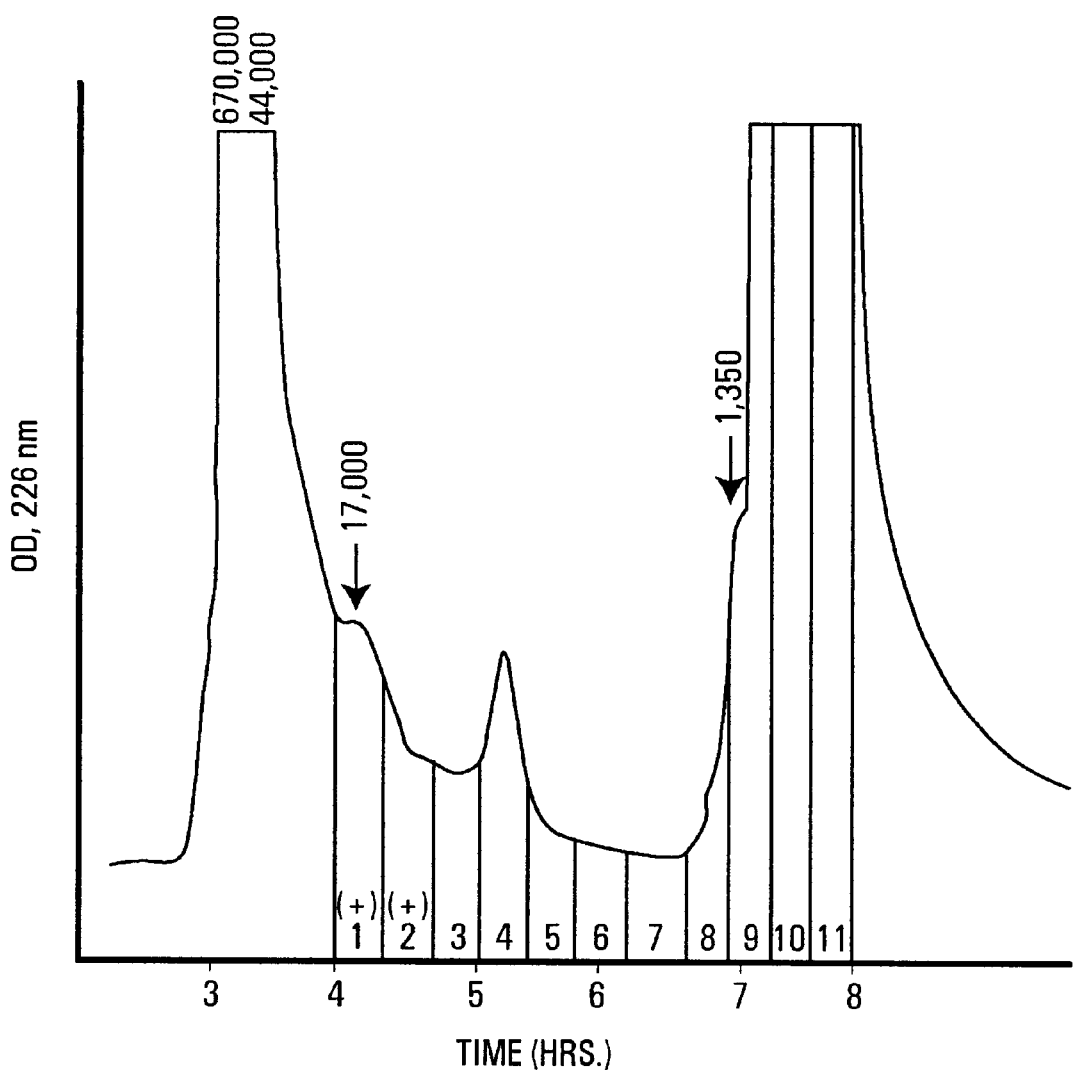
FIG. 1. Size-exclusion chromatogram of the 4.0 M GuHCl/10.0 mM Tris-HCl extract on Sephacryl S-100. The collected fractions are marked with the fraction number. The elution positions of globular protein standards, determined on a separate run, are shown (Bio-Rad MW standards: Thyroglobulin (bovine)—670,000; Ovalbumin (chicken)—44,000; Myoglobin (horse)—17,000; Cyanocobalamin—1,350.). Note the compression of the column and the virtual exclusion of proteins with $M_r$>50,000 so that the majority of the proteins in the extract eluted in the large void peak. Initial assays showed that the large void peak had no activity in the EMF [$^{35}$S]—SO$_4$-incorporation assay and these fractions were not collected routinely. Of the 11 retained fractions collected only fractions 1 and 2, marked +, showed activity.
Figure 3:
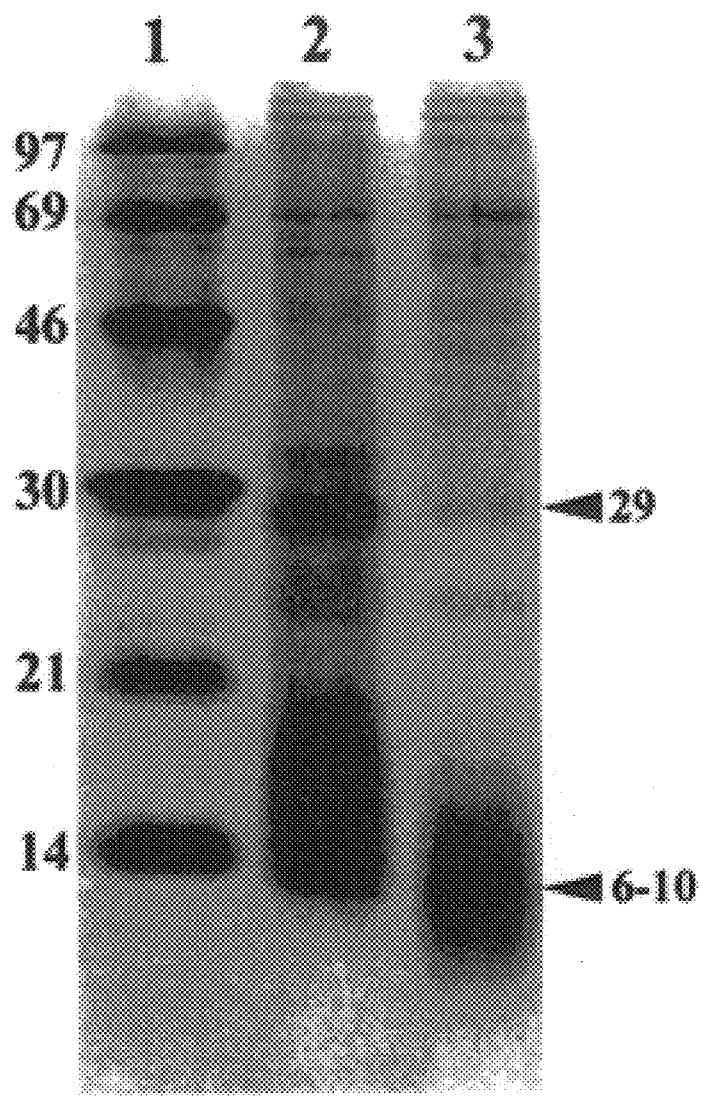

FIG. 3. Electrophoresis of the low molecular weight fractions obtained by chromatography of the 4.0 M GuHCl/10.0 mM Tris-HCl extract on Sephacryl S-100 denoted in FIG. 1, on a 15% SDS-polyacrylamide gel. Mercaptoethanol was present in the sample buffer. Components with $M_r$<18000 were the most prominent in both fractions. Lane 1—BioRad molecular weight standards. Lane 2—S-100 Fraction 1. Lane 3—S-100 Fraction 2.

Figure 4:
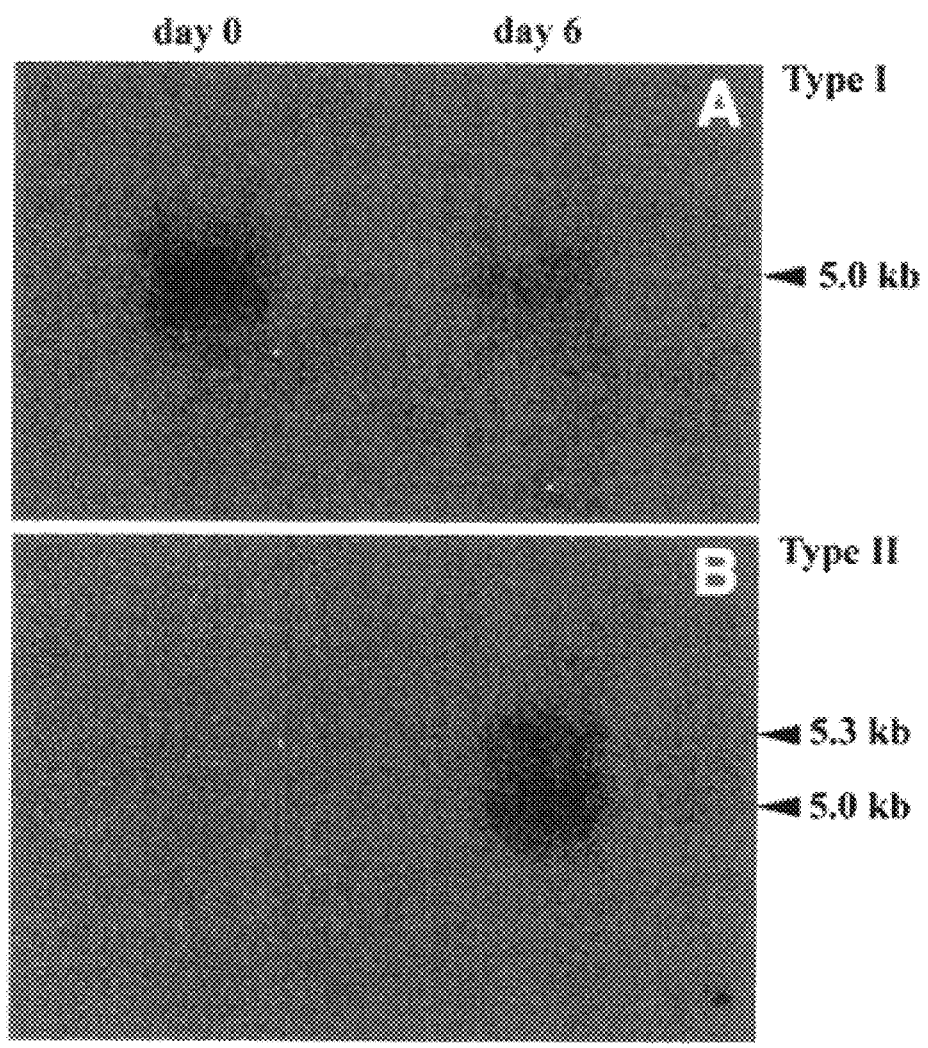

FIG. 4. Changes in expression of type I and type II collagen mRNAs in EMF upon culture in the continuous presence of the S-100 fraction, by Northern analysis. One μg EMF mRNA was loaded at day 0 and day 6 and electrophoresed on an agarose-formaldehyde minigel, transferred to Hybond –N membrane and probed. A- for type I collagen mRNA. B- for type II collagen mRNA. Note that 2 mRNA bands were evident for type II after 6 days The type II message was not detectable at day 0.

Figure 5:
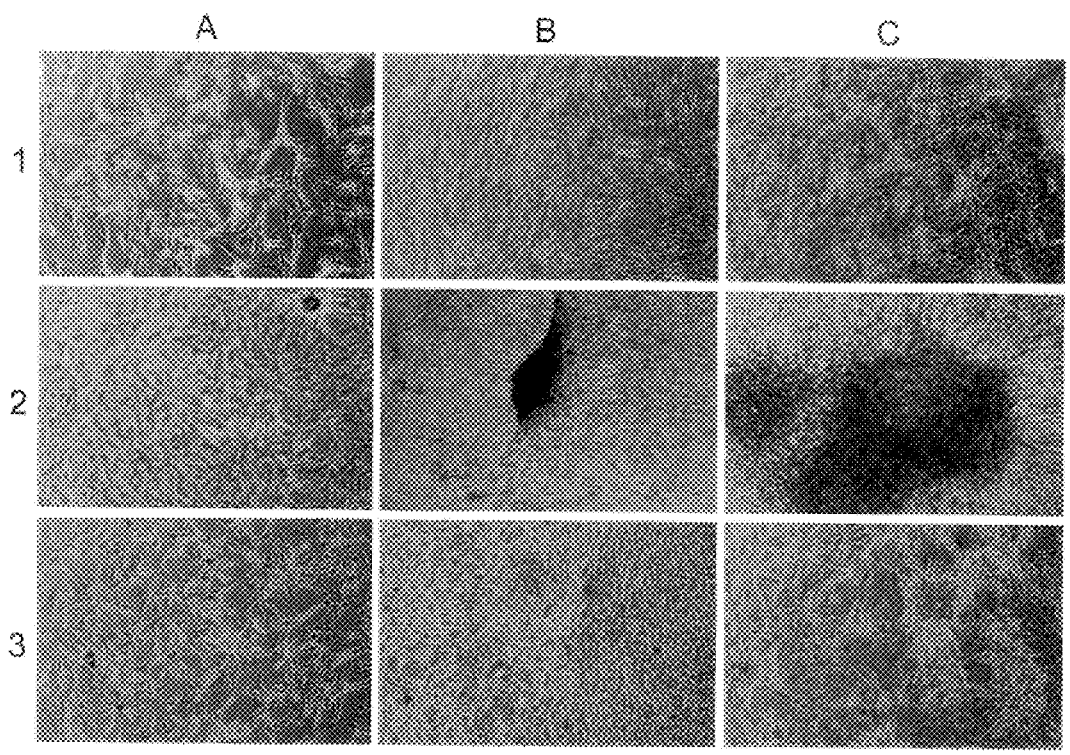

FIG. 5. Cell morphology and staining after monolayer culture of EMF with the putative chondrogenic agents for 49 days. Row 1, unstained cells. Row 2, cultures stained with Toluidine Blue (showing proteoglycan). Row 3, cultures stained with Alizarin Red (showing calcification). Column 1, control cultures, PBS/0.1% BSA, no factors added. Column 2, Bovine BMP (Urist), 200 μg/cm$^2$. Column 3, S-100, 100 μg/cm$^2$.

Figure 6:
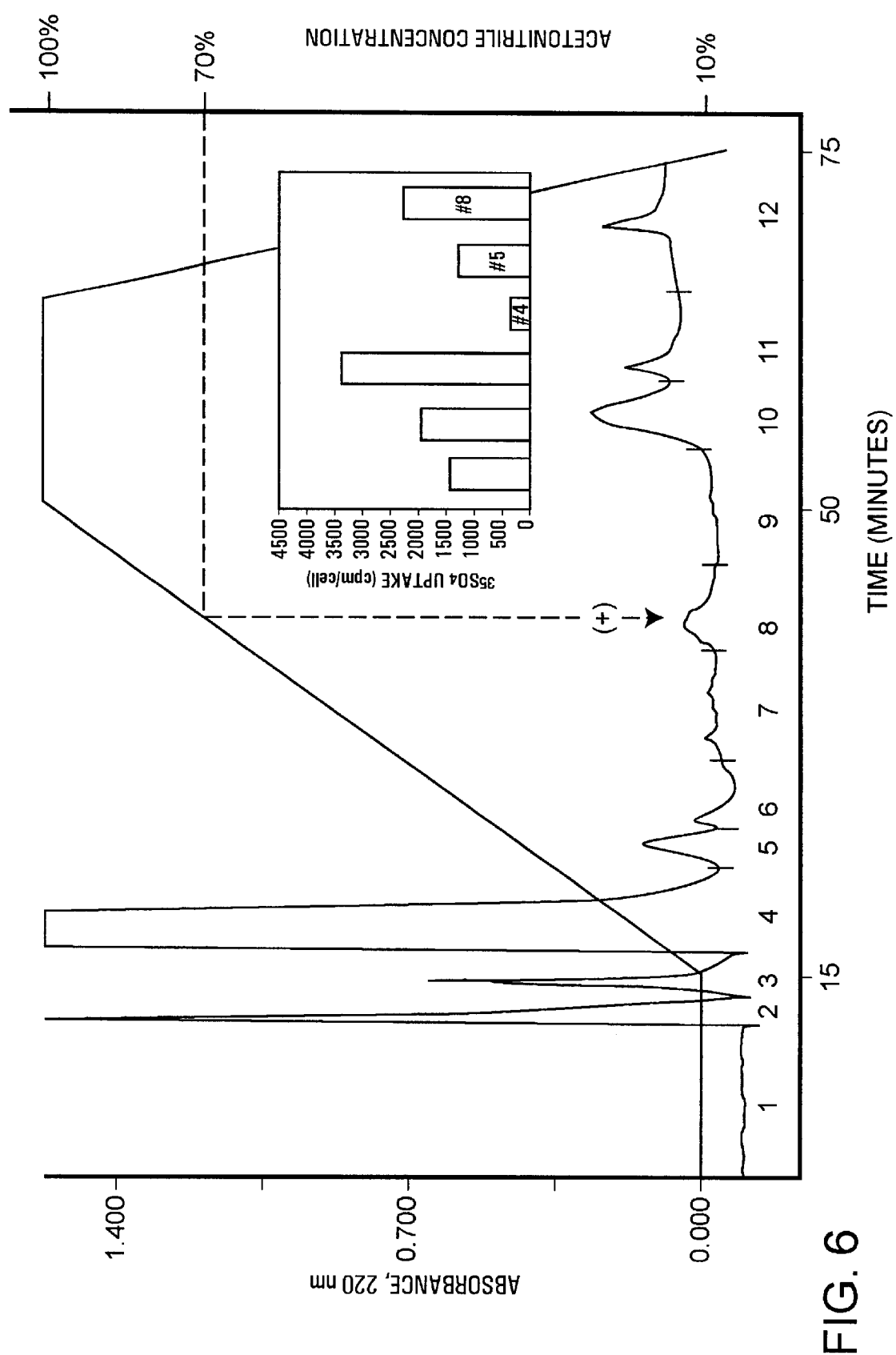

FIG. 6. First stage purification of S-100 by reverse phase chromatography on a Vydac C-18 semi-preparative column. The elution program covered 75 minutes. As shown by the solid straight lines, elution began with 15 min of 10% A-90% B, followed by a linear increase to 100% B over the next 35 min, followed by 100% B and return to 10% A-90% B as indicated. The eluate in each fraction, as numbered 1 to 12, was recovered and taken to dryness. A number of identical runs were required to accumulate sufficient material for the EMF [$^{35}$S]—SO$_4$-incorporation assay for the smaller peaks. The inset shows the result of the assay, using identical amounts of the test fractions. Fraction 5 was typical of the inactive peaks, equivalent to the PBS/0.1% BSA. Fraction 4, and 10 (data not shown) inhibited sulfate incorporation. Fraction 8, at 57.5 μg/ml was as active as rhBMP-2 at 100 ng/ml. Fraction 8 was the only active fraction. All of peak 8 was collected and combined from a number of runs, concentrated and run again under the same program. The major component was a single peak eluting at the same position. This was designated fraction 8b.

Figure 7:
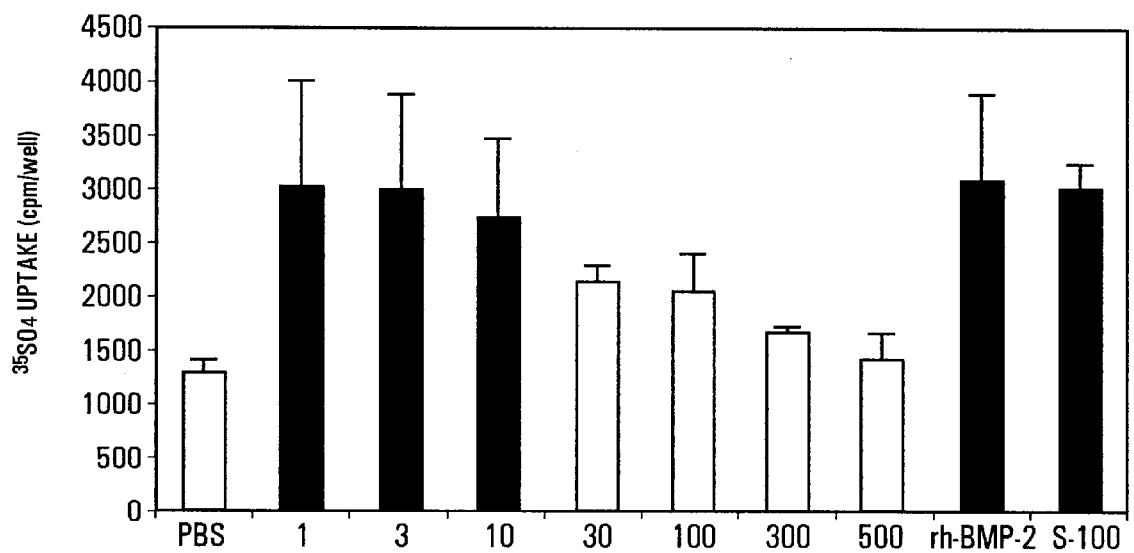

FIG. 7. Concentration dependence of sulfate incorporation activity of peak 8b from the semipreparative reverse phase chromatography. Negative control, PBS -PBS/0.1% BSA. Positive controls—rhBMP-2, 100 ng/ml; S-100, 1 mg/ml. Test concentrations for peak 8 in μg/ml. The activity in peak 8 was greater at higher dilutions.

Figure 8:
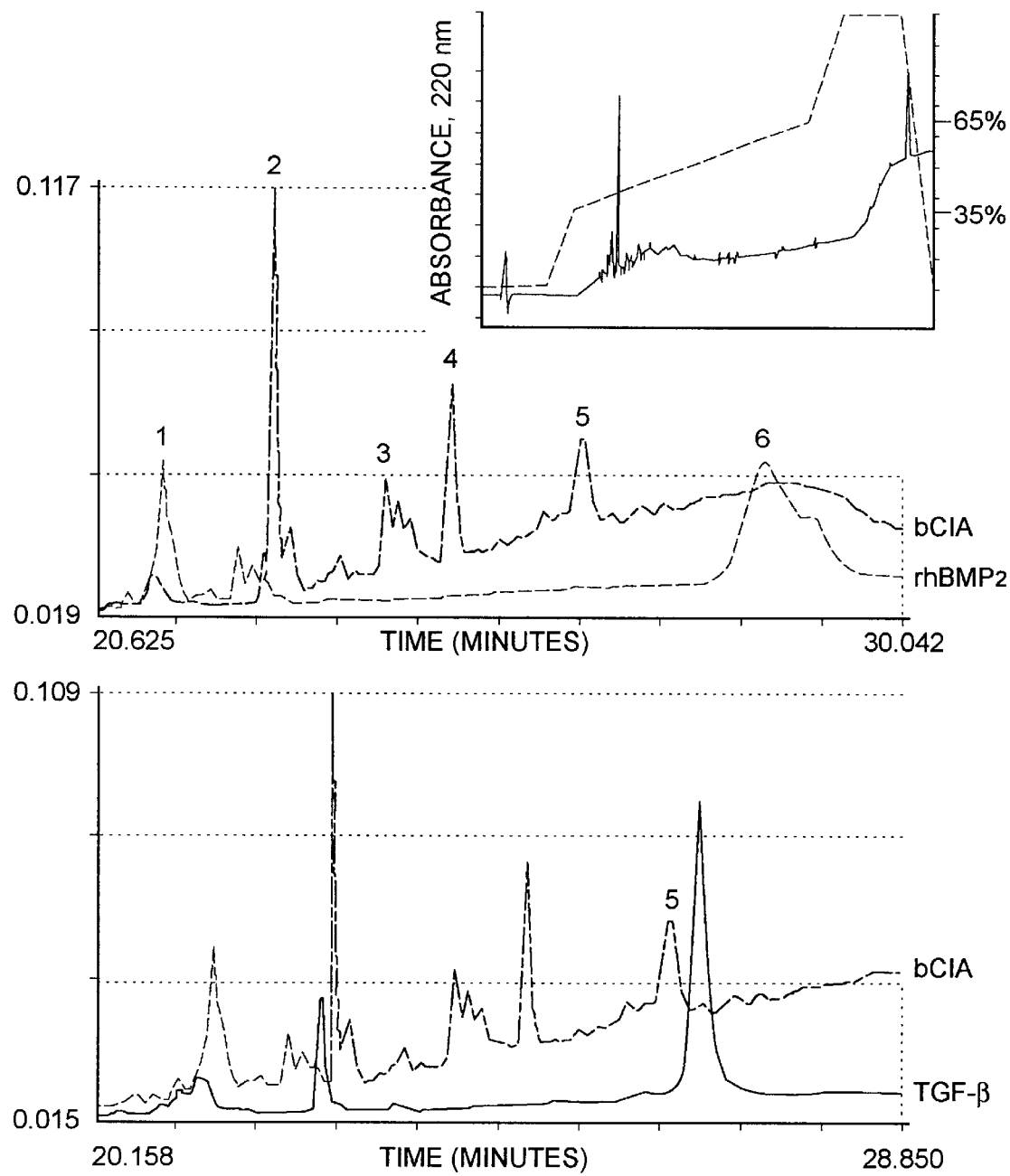

FIG. 8. Analytical scale reverse phase chromatography of peak 8b, on a Vydac C-18 column using a shallow gradient. Inset—The overall chromatogram of peak 8. The gradient program is shown by the straight lines. Upper plot- the dotted line with numbered peaks is the expanded chromatogram showing the components of peak 8. The dashed line is the chromatogram of rhBMP-2. Lower plot- the chromatogram of peak 8 compared with that of TGF-β. The EMF [$^{35}$S]—SO$_4$-incorporation activity was principally in peak 5, with a lesser activity in peak 6. Peak 5 was designated fraction 8b-5.

Figure 9:
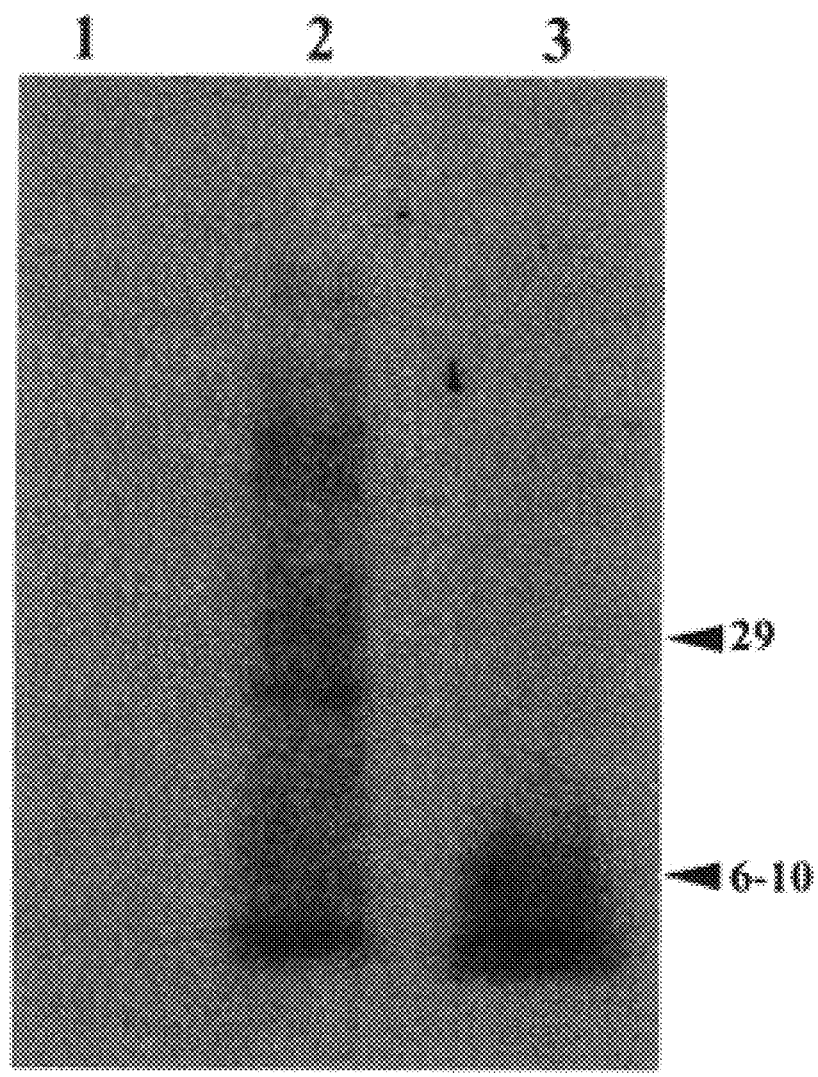

FIG. 9. Acrylamide gel electrophoresis of $^{125}$I-labeled fraction 8b-5. Lane 1- Molecular weight standards. Lane 2. Iodinated fraction S-100. Lane 3. Iodinated fraction 8b-5. The major component of 8b-5 is in the 6–10 K range of $M_r$.

Figure 10:
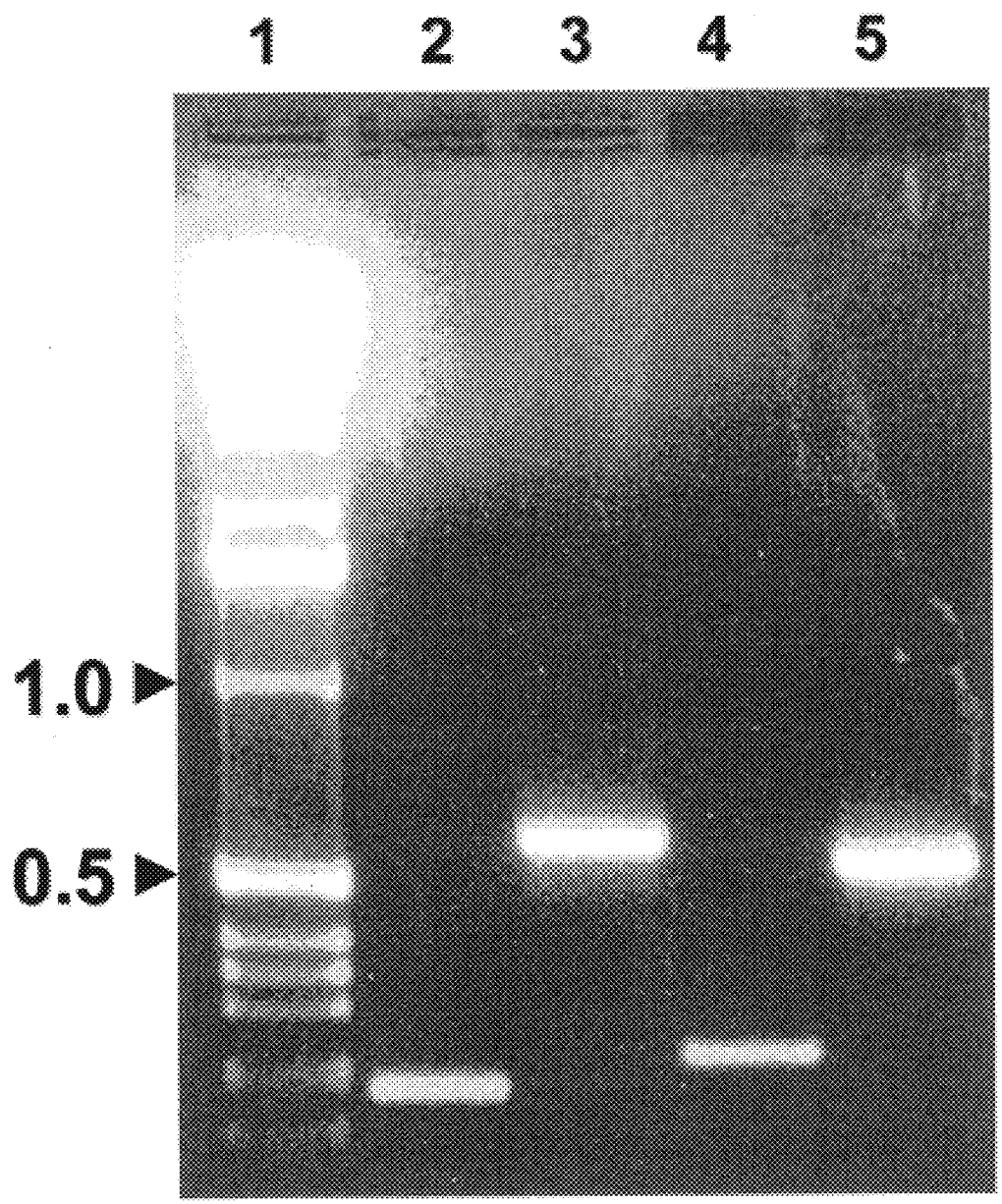

FIG. 10. Identification of the sizes of the full length amelogenin splice products obtained from the rat incisor tooth cDNA library. The amplified products are (A-4) (PCR200, Lane 2), A4 (PCR250, Lane 4), (B4) (PCR600, Lane 5) and B4 (PCR650, Lane 3). The PCR products were run on a 1% agarose gel and visualized by staining with ethidium bromide. Lane 1 was loaded with a 1 kb DNA ladder. Arrows indicate the 0.5 and 1 kb bands.

FIG. 11. The amelogenin gene alternative splice products detected in the rat incisor λgt11 cDNA library.

Figure 11A:
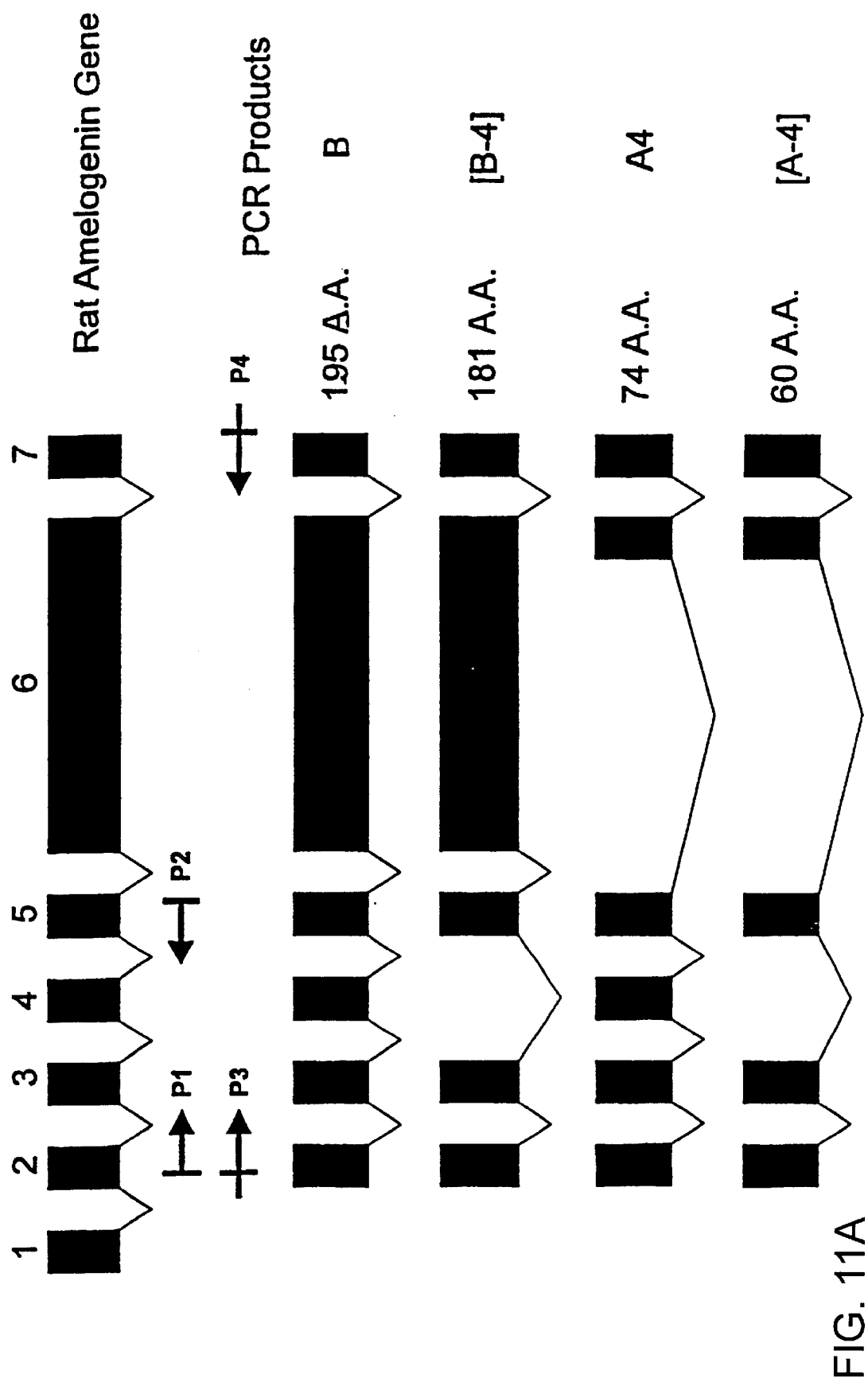

FIG. 11A. The exon-intron distribution in the rat amelogenin gene. The primers used initially to verify the presence of amelogenins in the library, P1 and P2, and the primers used to determine the specific splice products present, P3 and P4, are indicated. The exon designations follow the system of Simmer (1995). The number of amino acids encoded by each exon is shown within the exon box. The exon compositions of the PCR products, (B4), (B-4), (A4), (A-4), correspond to the bands shown in FIG. 10, lanes 3, 5, 4 and 2, respectively.

FIG. 11B. The nucleotide and amino acid compositions of (A4) (SEQ ID NO: 3 and SEQ ID NO: 4, respectively). The sequence of (A4) was determined to be identical to that shown for A4, except for the exclusion of exon 4 nucleotides and amino acids.

Figure 12:
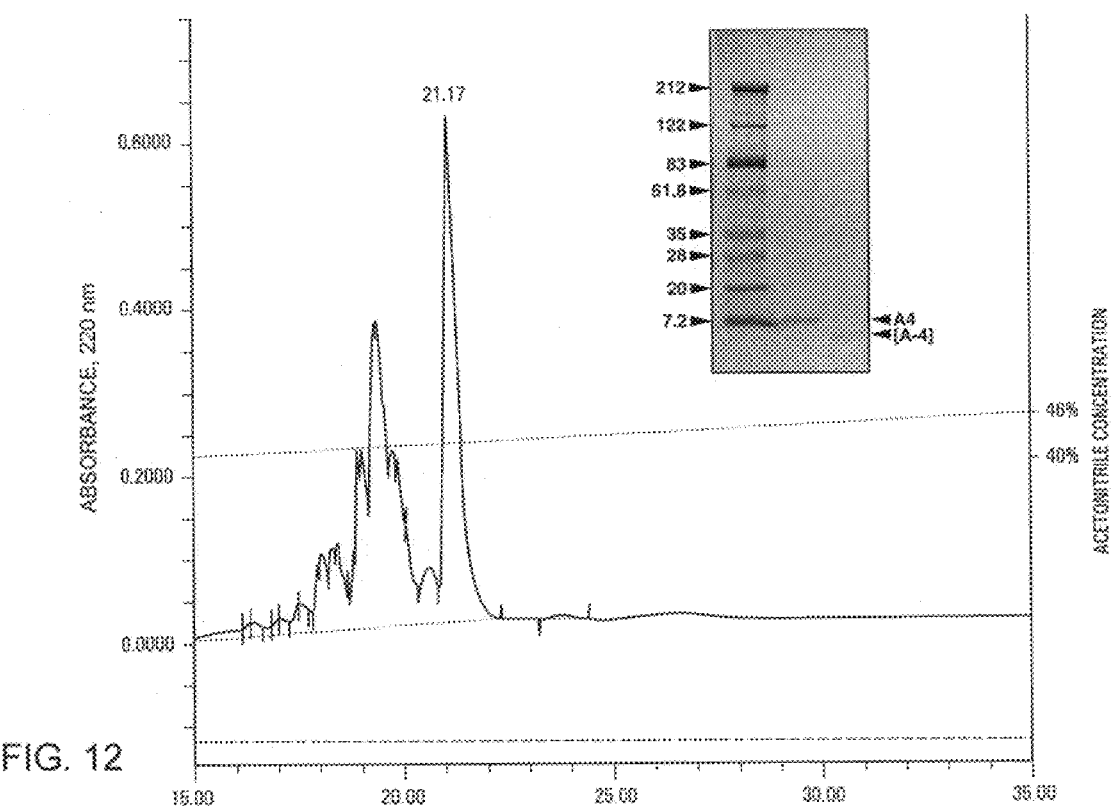

FIG. 12. HPLC purification of thrombin cleaved GST-fusion protein containing r(A-4). The inset shows the Coomassie stained gel of the final r(A4), peak obtained at 21.2 min. This homogeneous protein fraction was used for the bioassays. The rA4 was purified in the same manner.

Figure 13:
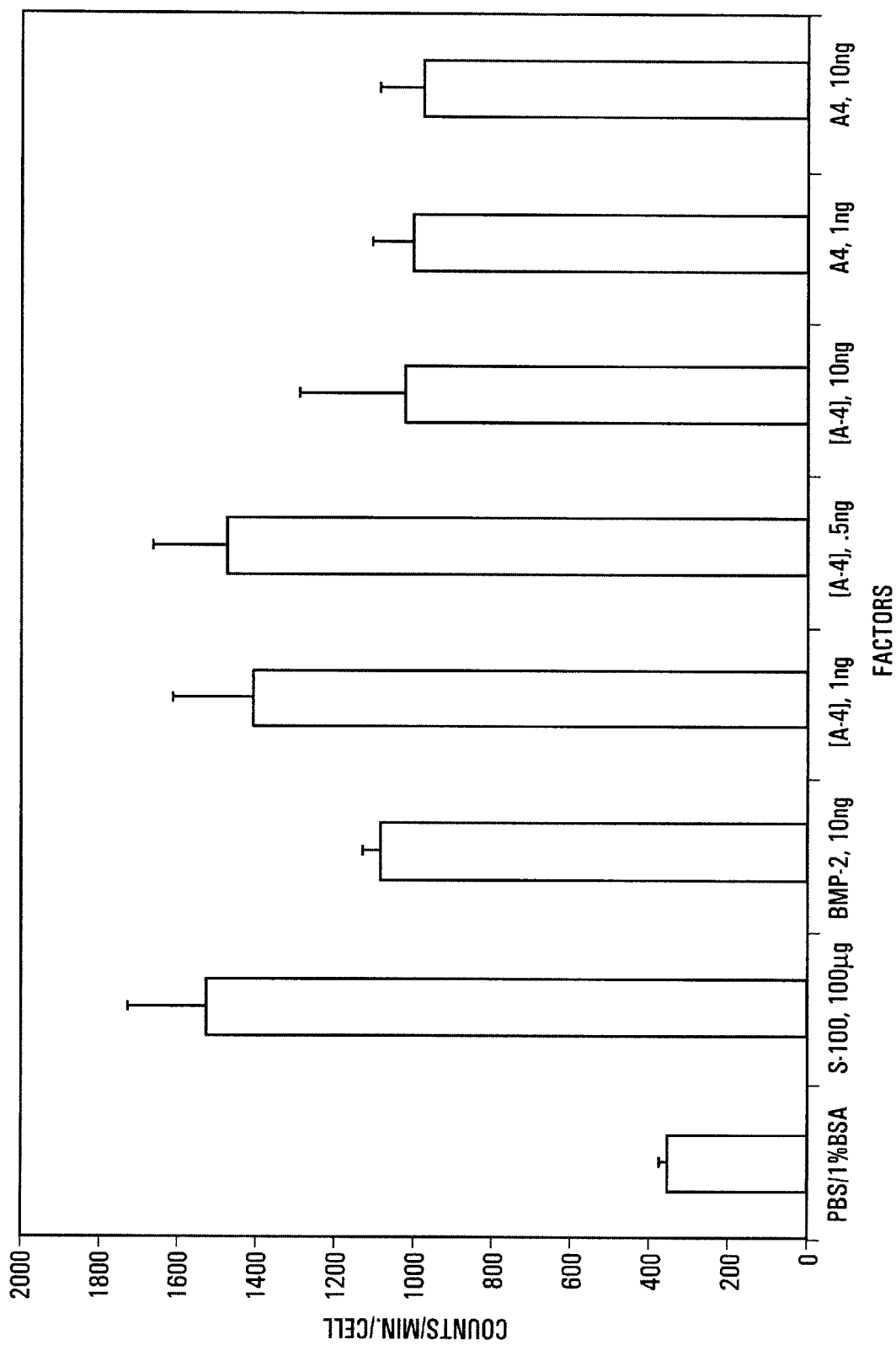

FIG. 13. In vitro assay for incorporation of $^{35}$S—SO$_4$ into rat embryonic muscle fibroblasts (EMF). The data represent five independent assays for each factor.

Figure 14:
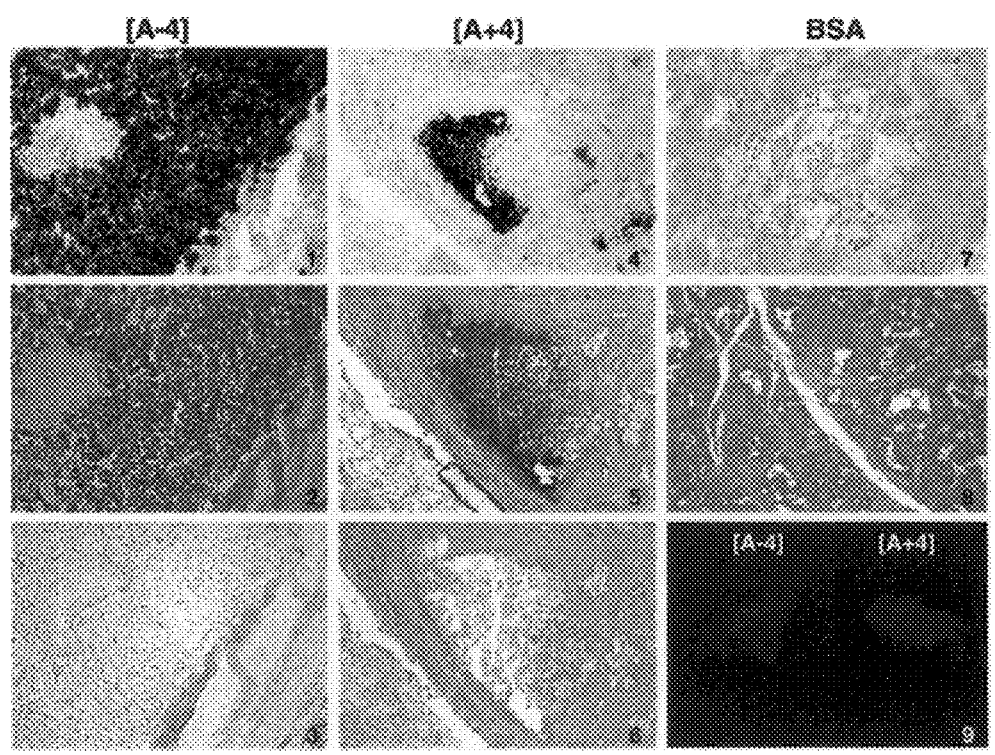

FIG. 14. In vivo assay for osteogenic, mineralization activity of A4 and (A-4). Numbers 1, 2 and 3 were taken from r(A-4) treated implants; 4,5 and 6 were from rA4 treated implants; and 7 and 8 were BSA implants. Numbers 1, 4 and 7 were Von Kossa stained; 2, 5 and 8 were Alizarin Red stained. Numbers 3 and 6 were EGTA- treated sections of (A-4) and A4, respectively. These data show that the (A-4) implants were highly positive for deposition of mineral, comparable to BMP2 implants (Whang et al. 1998). A4 had some focal deposits of mineral, and the BSA implant controls were negative. Number 9 shows the radiograph of the (A-4) and A4 implants immediately after excision and before processing for histology. Note the heavier mineralization around the periphery of the (A-4) implant in contrast to the more punctate deposition of mineral within A4.

Figure 15:
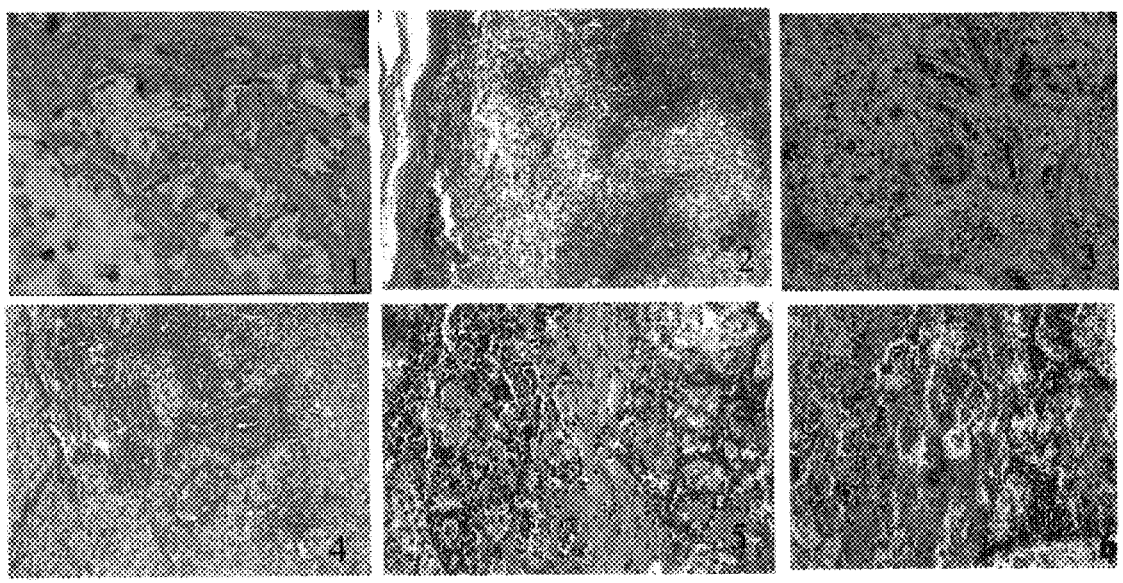

FIG. 15. Hematoxylin and Eosin stained sections of implants of r(A-4) and rA4 after 4 weeks. 1. Control negative, implant of poly(lactide)-poly(glycolide) scaffold containing BSA. The dense tissue at the upper portion of the micrograph is the connective tissue encapsulating the implant. Some of this tissue grows into the implant at the implant interface. The white, open areas are the implant scaffold. The intense vascularization of the implants is obvious. 2,3,4. Implants containing r(A-4) after 4 weeks. The scaffolds have been infiltrated by many cells, and an abundant network of capillaries. As seen in micrograph 2, a dense extracellular matrix has begun to form within the scaffold surrounding the capillaries. 5, 6. Implants containing rA4 after 4 weeks. The implants are vascularized but more sparsely than the r(A-4) implants. There is nevertheless, copious cellular infiltration. Micrograph 6, stained with Goldner's Trichrome stain, shows, in green, the forming extracellular matrix.

DETAILED DESCRIPTION OF THE INVENTION

The present invention relates to a polynucleotide that expresses a polypeptide having chondrogenic and osteogenic activity comprising the nucleotide sequence SEQ ID NO: 16. This polynucleotide corresponds to a splice product of the rat amelogenin gene encoded by rat amelogenin gene comprising exons 2, 3 ,4, 5, 6 and 7. Exon 6 of the rat amelogenin gene contains segments 6a, b, c and d.

In a preferred embodiment, the present invention provides a polynucleotide that expresses a polypeptide having chondrogenic and osteogenic activity wherein the polynucleotide encodes exons 2, 3, 4, 5, 6d and 7 in the rat amelogenin gene and has the sequence SEQ ID NO:1.

The present invention further relates to a polynucleotide that expresses a polypeptide having chondrogenic and osteogenic activity comprising the nucleotide sequence SEQ ID NO:17. This polynucleotide corresponds to a splice product of the rat amelogenin gene comprising exons 2, 3, 5, 6 and 7 of the rat amelogenin gene.

In a preferred embodiment, the polynucleotide encodes exons 2, 3, 5, 6d and 7 in the rat amelogenin gene and has the sequence SEQ ID NO:2.

The present invention also provides polypeptide molecules having chondrogenic and osteogenic activity. These polypeptides are related to the amelogenin family of proteins. Applicants have found that splice products of the amelogenin gene have chondrogenic/osteogenic activity.

Accordingly, the present invention provides polypeptides with in vitro chondrogenic and in vivo osteogenic activity. In one embodiment the polypeptide rA4 has the amino acid sequence SEQ ID NO:6. The polypeptide corresponds to the secreted form of a small alternative splice product of the rat amelogenin gene, with the amino acid sequence related to exons 2, 3, 4, 5, 6d and 7 in the rat amelogenin gene.

In another embodiment, the present invention provides a polypeptide with in vitro chondrogenic and in vivo osteogenic activity, polypeptide r(A-4) which has the amino acid sequence SEQ ID NO:5. The polypeptide corresponds to the secreted form of a small alternative splice product of the rat amelogenin gene, with the amino acid sequence related to exons 2, 3, 5, 6d and 7 in the rat amelogenin gene.

Another aspect of the present invention is directed to nucleic acid sequences complementary to the foregoing, or showing sequence similarity to, the DNA sequences identified in SEQ ID NOS: 1, 2, 16 and 17. The present invention is also directed to those sequences which are at least 60%, preferably at least 80%, and most preferably at least 95%, especially 98%, identical thereto, and to DNA (or RNA) sequences encoding the same polypeptide as the sequences of SEQ ID NOS: 5 and 6, including fragments and portions thereof and, when derived from natural sources, includes alleles thereof.

Amelogenins belong to the family of extracellular matrix proteins in developing tooth enamel and exhibit a high degree of conservation at the amino acid sequence level for bovine, mouse, pig and human species (Salido et al. 1992). Amelogenins are produced by ameloblasts and have been thought to play a role in enamel mineralization. No morphogenetic activities have been previously described for these molecules.

Thus, the present invention also relates to a human polypeptide that has chondrogenic and osteogenic activity, such polypeptide being a splice product of the expression of the human amelogenin gene (Simmer 1995). In one embodiment, the polypeptide is encoded by regions of the human amelogenin gene which correspond to exons 2, 3, 5, 6d and 7. In another embodiment, the polypeptide is encoded by regions of the human amelogenin gene which correspond to exons 2, 3, 4, 5, 6d and 7. In accordance with this aspect of the invention the polypeptides can be used to induce chondrogenesis and osteogenesis.

In a further aspect, the present invention also provides a polynucleotide that expresses in human a polypeptide having chondrogenic and osteogenic activity. In one embodiment the polynucleotide includes exons 2, 3, 5, 6d and 7 in the human amelogenin gene. In another embodiment the polynucleotide includes exons 2, 3, 4, 5, 6d and 7 in the human amelogenin gene.

The present invention is further directed to human amelogenin gene nucleic acid sequences complementary to the foregoing, or showing sequence similarity to, the DNA sequences that include exons 2, 3, 4, 5, 6d and 7 or 2, 3, 5, 6d and 7. The present invention is also directed to those sequences which are at least 60%, preferably at least 80%, and most preferably at least 95%, especially 98%, identical thereto, and to DNA (or RNA) sequences encoding the human polypeptide corresponding to the sequences of SEQ ID NOS: 5 and 6, including fragments and portions thereof and, when derived from natural sources, includes alleles thereof.

The present invention also provides a polynucleotide that expresses a bovine polypeptide having chondrogenic and osteogenic activity. In one embodiment the polynucleotide is encoded by exons 2, 3, 5, 6d and 7 in the bovine amelogenin gene which sequence has been described (Gibson et al., 1992). In another embodiment the polynucleotide is encoded by exons 2, 3, 4, 5, 6d and 7 in the bovine amelogenin gene.

In a still further aspect the invention also provides a bovine polypeptide which can be used to induce chondrogenesis and osteogenesis, said polypeptide encoded by the polynucleotide corresponding to exons 2, 3, 5, 6d and 7 of the bovine amelogenin gene. In another embodiment the polypeptide is encoded by the polynucleotide corresponding to exons 2, 3, 4, 5, 6d and 7 in the bovine amelogenin gene.

The invention further relates to degradation polynucleotides of the foregoing polynucleotides.

In accordance with the present invention, the term "percent identity" or "percent identical," when referring to a sequence, means that a sequence is compared to a claimed or described sequence after alignment of the sequence to be compared (the "Compared Sequence") with the described or claimed sequence (the "Reference Sequence"). The Percent Identity is then determined according to the following formula Percent Identity=100 [1-(C/R)] wherein C is the number of differences between the Reference Sequence and the Compared Sequence over the length of alignment between the Reference Sequence and the Compared Sequence wherein (i) each base or amino acid in the Reference Sequence that does not have a corresponding aligned base or amino acid in the Compared Sequence and (ii) each gap in the Reference Sequence and (iii) each aligned base or amino acid in the Reference Sequence that is different from an aligned base or amino acid in the Compared Sequence, constitutes a difference; and R is the number of bases or amino acids in the Reference Sequence over the length of the alignment with the Compared Sequence with any gap created in the Reference Sequence also being counted as a base or amino acid. If an alignment exists between the Compared Sequence and the Reference Sequence in which the percent identity as calculated above is about equal to or greater than a specified minimum Percent Identity then the Compared Sequence has the specified minimum percent identity to the Reference Sequence even though alignments may exist in which the hereinabove calculated Percent Identity is less than the specified Percent Identity.

The polynucleotides of the present invention may be in the form of RNA or in the form of DNA, which DNA includes cDNA, genomic DNA, and synthetic DNA. The DNA may be double-strrnded or single-stranded, and if single stranded may be the coding strand or non-coding (anti-sense) strand. The sequences which encodes the polypeptides may be identical to the sequences disclosed herein or may be a different coding sequence, which coding sequence, as a result of the redundancy or degeneracy of the genetic code, encodes the same polypeptide as the polynucleotide sequences of SEQ ID NOS: 1, 2, 16 and 17.

Tthe term "polynucleotide" as used for the present invention encompasses a polynucleotide which includes only coding sequence for the polypeptide as well as a polynucleotide which includes additional coding and/or non-coding sequences.

The present invention further relates to variants of the hereinabove described polynucleotides which encode fragments, analogs and derivatives of the polypeptides having the amino acid sequences of SEQ ID NOS: 5 and 6. Variants of the polynucleotide may be naturally occurring allelic variants of the polynucleotides or a non-naturally occurring variant of the polynucleotides.

As known in the art, an allelic variant is an alternate form of a polynucleotide sequence which may have a substitution, deletion or addition of one or more nucleotides, which does not substantially alter the function of the encoded polypeptide.

In accordance with the present invention, the term "gene" means the segment of DNA (or DNA segment) involved in producing a polypeptide chain; it includes regions preceding and following the coding region (5'-and 3'-untranslated regions, or UTRS, also called leader and trailer sequences, regions, or segments) as well as intervening sequences (introns) between individual coding segments (exons), which intronic regions are typically removed during processing of post-transcriptional RNA to form the final translatable mRNA product. Of course, by their nature, cDNAs contain no intronic sequences.

The DNA and RNA sequences, and polypeptides, disclosed in accordance with the present invention may be in isolated form. The term "isolated" means that the material is removed from its original environment (e.g., the natural environment if it is naturally occurring). For example, a naturally-occurring polynucleotide, or DNA, present in a living animal is not isolated, but the same polynucleotide or DNA, separated from some or all of the coexisting materials in the natural system, is isolated. Such DNA could be part of a vector and/or such polynucleotide could be part of a composition, and still be isolated in that such vector or polynucleotide is not part of its natural environment.

The DNA and RNA sequences, and polypeptides, disclosed in accordance with the present invention may also be in "purified" form. The term "purified" does not require absolute purity; rather, it is intended as a relative definition, and can include preparations that are highly purified or preparations that are only partially purified, as those terms are understood by those of skill in the relevant art. Individual clones isolated from a cDNA library have been conventionally purified to electrophoretic homogeneity. The cDNA clones are obtained via manipulation of a partially purified naturally occurring substance (messenger RNA). By conversion of mRNA into a cDNA library, pure individual cDNA clones can be isolated from the synthetic library by clonal selection. Thus, creating a cDNA library from RNA and subsequently isolating individual clones from that library results in an approximately $10^6$ fold purification of the native message. Purification of starting material or natural material to at least one order of magnitude, preferably two or three orders, and more preferably four or five orders of magnitude is expressly contemplated. Furthermore, claimed polynucleotide which has a purity of preferably 0.001%, or at least 0.01% or 0.1%; and even desirably 1% by weight or greater is expressly contemplated.

The term "coding region" refers to that portion of a human gene which either naturally or normally codes for the expression product of that gene in its natural genomic environment, i.e., the region coding in vivo for the native expression product of the gene. The coding region can be from a normal, mutated or altered gene, or can even be from a DNA sequence, or gene, wholly synthesized in the laboratory using methods well known to those of skill in the art of DNA synthesis.

In accordance with the present invention, the term "nucleotide sequence" refers to a heteropolymer of deoxyribonucleotides. Generally, DNA segments encoding the proteins provided by this invention are assembled from cDNA fragments and short oligonucleotide linkers, or from a series of oligonucleotides, to provide a synthetic gene which is capable of being expressed in a recombinant transcriptional unit comprising regulatory elements derived from a microbial or viral operon.

The term "expression product" means that polypeptide or protein that is the natural transcription product of the gene and any nucleic acid sequence coding equivalents resulting from genetic code degeneracy and thus coding for the same amino acid(s).

The term "fragment" when referring to a coding sequence means a portion of DNA comprising less than the complete human coding region whose expression product retains essentially the same biological function or activity as the expression product of the complete coding region. When referring to a portion of a polypeptide, as used herein, the terms "portion," "segment," and "fragment," refer to a continuous sequence of residues, such as amino acid residues, which sequence forms a subset of a larger sequence. For example, if a polypeptide were subjected to treatment with any of the common endopeptidases, such as trypsin or chymotrypsin, the oligopeptides resulting from such treatment would represent portions, segments or fragments of the starting polypeptide.

The term "primer" means a short nucleic acid sequence that is paired with one strand of DNA and provides a free 3'OH end at which a DNA polymerase starts synthesis of a deoxyribonucleotide chain. The term "promoter" means a region of DNA involved in binding of RNA polymerase to initiate transcription. The term "open reading frame (ORF)" means a series of triplets coding for amino acids without any termination codons and is a sequence (potentially) translatable into protein. The term "exon" means any segment of an interrupted gene that is represented in the mature RNA product.

As used herein, reference to a DNA sequence includes both single stranded and double stranded DNA. Thus, the specific sequence, unless the context indicates otherwise, refers to the single strand DNA of such sequence, the duplex of such sequence with its complement (double stranded DNA) and the complement of such sequence.

Using the sequence information provided herein, the polynucleotides of the present invention can be derived from natural sources or synthesized using known methods. The sequences falling within the scope of the present invention are not limited to the specific sequences described, but include human allelic and species variations thereof. Allelic variations can be routinely determined by comparison of one sequence with a sequence from another individual of the same species. Furthermore, to accommodate codon variability, the invention includes sequences coding for the same amino acid sequences as do the specific sequences disclosed herein. In other words, in a coding region, substitution of one codon for another which encodes the same amino acid is expressly contemplated. (Coding regions can be determined through routine sequence analysis.)

The present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including for example, a promoter, operably linked to the sequence. Large numbers of suitable vectors and promoters are known to those of skill in the art, and are commercially available. The following vectors are provided by way of example. Bacterial: pBs, phagescript, PsiX174, pBluescript SK, pBs KS, pNH8a, pNH16a, pNH18a, pNH46a (Stratagene); pTrc99A, pKK223-3, pKK233-3, pDR540, pRIT5 (Pharmacia). Eukaryotic: pWLneo, pSV2cat, pOG44, pXT1, pSG (Stratagene) pSVK3, pBPV, pMSG, pSVL (Pharmacia).

The present invention is not restricted to such constructs or sequences alone but also includes expression vehicles, which may include plasmids, viruses, or any other expression vectors, including cells and liposomes, containing any of the nucleic acids, nucleotide sequences, DNAs, RNAs, or fragments thereof, as disclosed according to the present invention.

A promoter region that may include a promoter different from that normally associated in vivo with the genes coding for the gene expression products and proteins disclosed according to the present invention. Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, and trc. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

The present invention relates to host cells containing the above-described construct(s). The host cell can be a higher eukaryotic cell, such as a mammalian cell, or a lower eukaryotic cell, such as a yeast cell, or the host cell can be a procaryotic cell, such as a bacterial cell. Introduction of the construct into the host cell can be effected by calcium phosphate transfection, DEAE, dextran mediated transfection, or electroporation (Davis, L., Dibner, M., Battey, I., Basic Methods in Molecular Biology, 1986)).

The constructs in host cells can be used in a conventional manner to produce the gene product coded by the recombinant sequence. Alternatively, the encoded polypeptide, once the sequence is known from the cDNAs, or from isolation of the pure product, can be synthetically produced by conventional methods of peptide synthesis, either manual or automated. In accordance with the present invention, once the coding sequence is known, or the gene is cloned which encodes the polypeptide, conventional techniques in molecular biology can be used to obtain the polypeptide. More generally, the present invention includes all polypeptides coded for by any and each of the DNA or RNA sequences disclosed herein, including fragments of said polypeptides, as well as derivatives and functional analogs thereof.

The amino acid sequence can be synthesized using commercially available peptide synthesizers. This is particularly useful in producing small peptides and fragments of larger polypeptides. (Fragments are useful, for example, in generating antibodies against the native polypeptide.) Alternatively, the DNA encoding the desired polypeptide can be inserted into a host organism and expressed. The organism can be a bacterium, yeast, cell line, or multicellular plant or animal. The literature is replete with examples of suitable host organisms and expression techniques. For example, polynucleotide (DNA or mRNA) can be injected directly into muscle tissue of mammals, where it is expressed. This methodology can be used to deliver the polypeptide to the animal, or to generate an immune response against a foreign polypeptide. Wolff, et al., *Science*, 247:1465 (1990); Felgner, et al., *Nature*, 349:351 (1991). Alternatively, the coding sequence, together with appropriate regulatory regions (i.e., a construct), can be inserted into a vector, which is then used to transfect a cell. The cell (which may or may not be part of a larger organism) then expresses the polypeptide.

The terms "fragment," "derivative" and "analog," when referring to the polypeptides disclosed herein also mean polypeptides that retain essentially the same biological function or activity as said polypeptides. Thus, an analog includes a proprotein which can be activated by cleavage of the proprotein portion to produce an active mature polypeptide. Such fragments, derivatives and analogs must have sufficient similarity to the polypeptides disclosed herein so that activity of the native polypeptide is retained.

The polypeptides of the present invention may be recombinant polypeptides, natural polypeptides or synthetic polypeptides, preferably recombinant polypeptides. "Recombinant," as used herein, means that a protein is derived from recombinant (e.g., microbial or mammalian) expression systems. "Microbial" refers to recombinant proteins made in bacterial or fungal (e.g., yeast) expression systems. As a product, "recombinant microbial" defines a protein essentially free of native endogenous substances and unaccompanied by associated native glycosylation. Protein expressed in most bacterial cultures, e.g., E. coli, will be free of glycosylation modifications; protein expressed in yeast will have a glycosylation pattern different from that expressed in mammalian cells.

The fragment, derivative or analog of a polypeptide of SEQ ID NOS: 5 or 6 may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the abilities of those skilled in the art in view of the teachings herein.

The polypeptides of the present invention are preferably provided in an isolated form, and preferably are purified to homogeneity. When applied to polypeptides, the term "isolated" has its already stated meaning.

The polypeptides of the present invention include the polypeptides of SEQ ID NOS: 5 and 6, as well as polypeptides which have at least 70% identity to these polypeptides, or which have, at least 90% identity to these polypeptides, still more preferably at least 95% identity to these polypeptides.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention.

The present invention also relates to vectors which include polynucleotides of the present invention, host cells which are genetically engineered with vectors of the invention and the production of polypeptides of the invention by recombinant techniques. Host cells are genetically engineered (transduced or transformed or transfected) with the vectors of this invention which may be, for example, a cloning vector or an expression vector, either of which may be in the form of a plasmid, a viral particle, a phage, etc. The engineered host cells can be cultured in conventional nutrient media modified as appropriate for activating promoters, selecting transformants or amplifying the genes of the present invention. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host. In accordance with the present invention, an appropriate DNA sequence or segment may be inserted into the vector by a variety of procedures. In general, the DNA sequence is inserted into the appropriate restriction endonuclease site(s) by procedures known in the art. Such procedures and others are deemed to be within the scope of those skilled in the art.

The DNA sequence in the expression vector is operatively linked to an approprate expression control sequences) (for example, a promoter sequence) to direct MRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression. In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli. The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhirnurium; fingal cells, such as yeast; insect cells such as Drosophila S2 and Spodoptera Sf9; animal cells such as CHO, COS or Bowes melanoma; adenoviruses; plant cells, etc. The selection of an appropriate host is deemed to be within the scope of those skilled in the art from the teachings herein.

"Recombinant expression vehicle or vector" refers to a plasmid or phage or virus or vector, for expressing a polypeptide from a DNA (RNA) sequence. The expression vehicle can comprise a transcriptional unit comprising an assembly of (1) a genetic element or elements having a regulatory role in gene expression, for example, promoters or enhancers, (2) a structural or coding sequence which is transcribed into mRNA and translated into protein, and (3) appropriate transcription initiation and termination sequences. Structural units intended for use in yeast or eukaryotic expression systems preferably include a leader sequence enabling extracellular secretion of translated protein by a host cell. Alternatively, where recombinant protein is expressed without a leader or transport sequence, it may include an N-terminal methionine residue. This residue may or may not be subsequently cleaved from the expressed recombinant protein to provide a final product.

"Recombinant expression system" means host cells which have stably integrated a recombinant transcriptional unit into chromosomal DNA or cany the recombinant transcriptional unit extra chromosomally. The cells can be prokaryotic or eukaryotic. Recombinant expression systems as defined herein will express heterologous protein upon induction of the regulatory elements linked to the DNA segment or synthetic gene to be expressed.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryatic and eukaryotic hosts are described by Sambrook, et al., *Molecular Cloning: A Laboratory Manual*, Second Edition, (Cold Spring Harbor, N.Y., 1989), Wu et al, *Methods in Gene Biotechnology* (CRC Press, New York, N.Y., 1997), and *Recombinant Gene Expression Protocols*, in *Methods in Molecular Biology*, Vol. 62, (Tuan, ed., Humana Press, Totowa, N.J., 1997), the disclosures of which are hereby incorporated by reference.

Transcription of the DNA encoding the polypeptides according to the present invention by higher eukarotes can be increased by insertion of an enhancer sequence into the vector. Such enhancers have been known for some time and are usually cis-acting elements of DNA, usually anywhere from 10 to 300 bp that act on a promoter to increase transcription. Common examples include the SV40 enhancer, the cytomegalovirus early promoter enhancer, the polyoma enhancer and the enhancers found in adenovirus.

Generally, recombinant expression vectors will include origins of replication and selectable markers permitting transformation of the host cell, e.g., the ampicillin resistance gene of *E. coli* and *S. cerevisiae* TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM 1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is derepressed by appropriate means (e.g., temperature shift or chemical induction) and cells are cultured for an additional period. Cells are typically harvested by centrifugation, disrupted by physical or chemical means, and the resulting crude extract retained for further purification.

Various mammalian cell culture systems can also be employed to express recombinant protein. Examples of mammalian expression systems include the COS-7 lines of monkey kidney fibroblasts, described by Gluzman, *Cell*, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 viral genome, for example, SV40 origin, early promoter, enhancer, splice, and polyadenylation sites may be used to provide the required nontranscribed genetic elements.

Recombinant protein produced in bacterial culture is conveniently isolated by initial extraction from cell pellets, followed by one or more salting-out, aqueous ion exchange or size exclusion chromatography steps. Protein refolding steps can be used, as necessary, in completing configuration of the mature protein. Finally, high performance liquid chromatography (HPLC) can be employed for final purification steps. Microbial cells employed in expression of proteins can be disrupted by any convenient method, including freeze-thaw cycling, sonication, mechanical disruption, or use of cell lysing agents.

The chondrogenic/osteogenic inducing molecule(CIM), also known as chondrogenic inducing agent (CIA), has been isolated from the 4.0 M guanidinium hydrochloride extract of demineralized, defatted, bovine dentin extracellular matrix. Dentin matrix is known to contain components capable of inducing chondrogenesis and osteogenesis at ectopic sites when implanted in vivo, and chondrogenesis in cultures of embryonic muscle-derived fibroblasts (EMF) in vitro. Following Sephacryl S-100 chromatography, activity (bCIA) was identified in fractions by assay for uptake of [$^{35}$S]—SO$_4$ into proteoglycan by the EMF after 24 hours in culture. The active S-100 fraction induced the EMF to produce type II collagen mRNA and decrease production of type I collagen mRNA after 5 days in culture. The EMF cultures+bCIA for 4 to 7 weeks condensed into Toluidine Blue and Alizarin Red stainable nodules, changes indicative of chondrogenic induction. In vivo implants in rat muscle with collagen carrier produced ectopic bone after 7 weeks. The bCIA was brought to near homogeneity by several rounds of reverse phase high performance liquid chromatography, tested at each step by EMF [$^{35}$S]—SO$_4$ incorporation assays.

The reverse phase HPLC protocols led to the isolation of a bioactive peptide fraction with activity at the ng/ml level. Gel electrophoresis of the I25I-derivatized purified fraction showed it to contain peptides within the M$_r$ range of 6,000 to 10,000 (FIG. 9). This molecular mass was also consistent with mass spectroscopic determinations, which placed peptides at 6,797 and 10,607 D as prominent components of a partially purified preparation.

A striking feature of the isolated peptide fraction was the amino acid composition. The peptide was proline and leucine rich and devoid of cysteine, ruling out the possibility that the peptide had been derived from the BMP/TGF-β family. Amino terminal sequencing of the peptide by Edman degradation of tryptic fragments of the fraction 8b-5, led to the identification of the bioactive peptide(s) as arising from, or containing the amino-terminal domain of bovine amelogenin (Gibson et al. 1992).

The peptides having sequences SEQ ID NO:7 and SEQ ID NO:8 (amino acids 1–5 and 25–30, respectively, of the amelogenin sequence) were recovered in the tryptic digest. SEQ ID NO:7 was clearly at the N-terminal of the secreted form of the amelogenin, and SEQ ID NO:8 follows the first internal Lys residue of the 176 amino acid residue form of the bovine amelogenin.

The peptide sequences were used to generate PCR primers and full length reverse transcribed cDNAs for 2 amelogenins cloned from a fetal rat dentin library. The cDNAs were transduced in $E.coli$ and the two amelogenins produced in the BL21 expression system. The amelogenin proteins were purified by HPLC.

Analysis of purified recombinant amelogenins A4 (rA4) and A4 (r(A-4)) confirmed that the amelogenin peptides have specific biological activities, equivalent to rBMP-2, in directing the change in phenotype of the embryonic rat muscle fibroblasts in vitro and inducing the onset of osteogenesis in muscle implants in vivo. These specific small amelogenin gene splice products can influence the differentiation of embryonic or stem cells and modulate aspects of their phenotypic expression.

Thus, the polypeptides may be employed as chondrogenic and osteogenic enhancing factors. Accordingly, the polypeptides may be used in a method for enhancing the differentiation of stem cells by contacting cells in vitro or in vivo. Alternatively the polypeptides may be placed in contact with areas of potential connective tissue growth or connective tissue damage to enhance or stimulate growth in vivo for regeneration and or repair. Using these methods synthesis of bone matrix or articular surfaces at or near implant sites may be enhanced and can be initiated in a controlled and uniform manner.

Specific embodiments of the invention will now be further described in more detail in the following non-limiting examples and it will be appreciated that additional and different embodiments of the teachings of the present invention will doubtless suggest themselves to those of skill in the art and such other embodiments are considered to have been inferred from the disclosure herein.

EXAMPLES

Materials and Methods
Biological Activity Assay
Embryonic Muscle Fibroblast (EMF) Tissue Culture Assay Embryonic Muscle Fibroblasts. Rat EMF cells were derived from the thigh muscles of 20 day old Sprague Dawley rat embryos for use in primary tissue culture assays using a modification of the Koskinen harvesting technique (Koskinen et al., 1985), and grown in growth media (GM) [α-Modified Eagle's Medium (αMEM , Life Technologies, Gaithersburg, Md.), containing 10% heat inactivated fetal bovine serum (FBS), 1% Penicillin/Streptomycin (P/S)] in 5% $O_2$/95% air at 37° C. EMFs were frozen at passage 2 (P-2).

Short Term Culture and Labeling with $^{35}SO_4$—Sulfate. The EMFs were plated (day 0) at a concentration of $10^4$ cells per well in a 96 well plate which had been precoated with 100 μl of a 50 μg/ml solution of type I Rat Tail Collagen (Collaborative Biomedical Products). The cells were grown for 5 days in GM. On day 5, the cells were conditioned by removing the GM and adding conditioning media (CM) (αMEM containing 0.5% FBS, 1 % P/S) for 24 hours. This media was replaced with 100 μl of fresh CM, just prior to the addition of the test factors (hour 0). Test factors were added to test wells in triplicate. PBS/0. 1% BSA alone served as a negative control. rhBMP-2 (a gift from Genetics Institute, Boston, Mass.) and demineralized dentin, suspended in PBS/0. 1% BSA, were used as positive controls. Four hours following the addition of factors, the cells were labeled with 1 μCi $^{35}S$—$SO_4$/10 μl sterile PBS/well/96 well plate for 20 hours.

Assay of $^{35}S$ Sulfate Incorporation Into Proteoglycans in the Medium. In a departure from the Koskinen et al. (1985) protocol, glycosaminoglycan synthesis was routinely determined by the measurement of incorporation of $^{35}S$ sulfate (ICM Biomedical, Costa Mesa, Calif.) into the total cetylpyridinium chloride (CPC)-precipitable materials in the media without prior papain digestion. Deletion of the digestion steps shortened the analyses time and improved the reproducibility of the analyses. The total medium from each well (~115 μl) was placed into a 13×100 mm glass culture tube. 150 μl of 100 μg/ml Chondroitin Sulfate A Sodium Salt (Sigma, St. Louis, Mo.) at 4° C. (buffer C), was added to each tube to serve as a carrier. 500 μl of 2.0 mM $MgSO_4$, 4° C. (buffer B), was added. The mixture was incubated in a 37° C. water bath with shaking for 30 minutes. One ml of 1% CPC in 0.02M NaCl (buffer D) was added and incubated at 37° C. for 60 minutes in the water bath.

The samples were filtered through Whatman GF/A glass microfibre filters using a Millipore 12 well filtration device. The contents of each glass tube were individually poured into one of the wells under suction. The tube and filters were washed with buffer B 3 times. The filters were allowed to dry briefly, and were transferred to a scintillation vial. Then 5 ml scintillation cocktail was added per vial and the radioactive counts were measured in the scintillation counter.

Cell Shape Changes, Monolayer Culture of EMFs on bCIA Coated Plates-Long Term. To test the activity of the bCIA protein in contact with the EMF cells over time, the procedure of Iwata et al. (1993) was used. Aliqupts of bCIA protein were dissolved in deionized $H_2O$ ($dH_2O$) at various concentrations and then coated onto tissue culture dishes by drying the protein and sterilizing using UV light. The EMF cells were added in GM and grown in GM with media changes every other day for up to 49 days in culture. The cell morphology was followed with light microscopic photographs every few days. Morphological changes were assessed at the light microscopical level throughout 49 days in culture, and the final cultures were fixed and stained using either alcian blue, toluidine blue, or alizarin red. Sets of control cell cultures grown in medium without any additions were also stained. Three concentrations of bCIA (pooled S-100, fractions #1 and 2, see below), 100, 200, and 500 μg/$cm^2$ were tested, as were 100 and 200 μg/$cm^2$ of crude bovine BMP (a generous gift from Dr. Urist).

Alcian Blue Staining—The cells were fixed with 100% methanol for 15 minutes, and then stained with 0.1% Alcian Blue 8GX (Sigma) stain in 0.1 N HCl, for 2–24 hours at 25° C. The Alcian Blue stain was filtered through 0.45 μm filter paper prior to use. The cells were washed with water, then photographed.

Toluidine Blue Staining—The cells were fixed with 100% methanol overnight. The cells were stained with 0.04% Toluidine Blue (Sigma), which was prepared and then filtered through a 0.45 μm filter paper to remove undissolved particles, for 30 minutes.

Alizarin Red Staining—A solution of 1% Alizarin Red S (Sodium Alizarin Sulfonate, Sigma), in $dH_2O$ was made and adjusted to pH 6.4 with 0.1 N ammonium hydroxide solution. Following fixation with 100% methanol, the cells were stained with the Alizarin Red S solution for 15 minutes to overnight, and then washed with $dH_2O$, and photographed.

Phenotypic Changes in EMF Expression. To determine if the cell morphological changes were consistent with potential cartilage production and altered cell phenotype, the EMF were grown to confluence in collagen coated T75 flasks in GM, then, after washing with CM, for 6 days in fresh CM containing 1 mg/ml of active fraction protein ($^{35}S$—$SO_4$-incorporation) from the Sephacryl S-100 (Pharmacia, Piscataway, N.J.) chromatography (see below). The cell layer was collected by trypsinization, and the mRNA isolated using the InVitrogen Fast Track mRNA Isolation kit according to the manufacturers instructions. One microgram mRNA was electrophoresed in a formaldehyde denaturing gel and then transferred to Nylon membrane. The membrane was hybridized with Type I and Type II collagen probes. Controls were run with 0.1 % BSA/PBS added to the cultures in place of the active fractions. Cultures were examined at day 0 and day 6. The type I probe (pHF677 ($\alpha1(I)$)), contained a 1.8 kb cDNA clone hybridizing to the nucleotides corresponding to the sequence from amino acid residue 787 to 270 nucleotides into the 3' untranslated region of the pro $\alpha1(I)$ mRNA (A kind gift from Dr. Linda Sandell, Washington University). The type II probe (p1377 ($\alpha1(II)$)) (Kohno et al., 1984) contained a 550 bp clone coding for the amino terminal portion of the rat pro $\alpha1(II)$ chain.

Bone Formation In Vivo. Implantation in Muscle

For implantation, 25 μg S-100 or 35 ng rhBMP-2 in 200 μl of PBS/0.1% BSA were absorbed onto 0.45 mg rat tail tendon collagen and lyophilized. The coated collagen was sterilized, then placed into sterile 5 mm gelatin capsules. Capsules were prepared with the collagen only as a negative control. Demineralized insoluble dentin matrix was used as a positive control. A 1 cm incision was made and a small intramucscular pouch was created by blunt dissection into the thigh muscle of the hind limbs of 100 g (4 week old) Long-Evans rats. The capsules were inserted, then the fascia was closed using 4-0 Vicryl sutures. The skin was closed with 4-0 silk sutures. All protocols for anesthesia, surgery, recovery, care and euthanasia were approved by the Northwestern University Animal Care and Use Committee. All test samples were implanted in the right thigh, all negative collagen controls in the left. At nine weeks, the animals were euthanized and the tissues were collected and prepared for histologic examination, using the von Kossa stain for the presence of mineral deposition.

Example 1

CIM Isolation

Bovine Teeth Isolation and Preparation. Heads were obtained at the abattoir (Chiappetti Packing House, Chicago) from 5 month old animals, and immediately placed on ice. All teeth were removed from the heads, cleaned of adherent bone, periodontal ligament, and soft tissue, and placed in a 15% NaCl wash solution containing 50.0 mM Tris.HCl, pH 7.5, 20.0 mM Ethylenediaminetetraacetic acid (EDTA), and protease inhibitors (PIs) including 2.5 mM Benzamidine HCl, 50.0 mM ε-Amino-n-Caproic Acid, 0.5 mM N-Ethylmaleimide (NEM), and 0.3 mM Phenylmethylsulfonyl Fluoride (PMSF) at 4° C. The pulpal tissues were removed and the teeth were pulverized into small particles in a Spex 6700 Freezer/Mill at liquid nitrogen temperature, and stored at −80° C.

Demineralization. The tooth particles were washed in 5.0 mM sodium azide (NaN3) and demineralized in 0.6 N HCl plus 1 μg/ml Pepstatin A at 4° C. with continuous stirring for 5 days.

Sequential Extraction. The following extractions (Urist et al., 1987) and treatments were performed in sequential order, with washes of $dH_2O$ containing PIs, at 4° C. between steps. The pulverized tooth powder was defatted in a 1:1 (v/v) chloroform/methanol solution for 1 hour at 25° C., then extracted in 2.0 M $CaCl_2$ with PIs for one hour at 4° C. The remaining liquid was decanted, and the tooth powder extracted in 0.5 M EDTA with PIs, pH 7.4, at 4° C. for 1 hour, followed by 8.0 M LiCl, pH 5.5, with PIs at 4° C. with stirring for 1 hour, then $dH_2O$ containing PIs in a 55° C. $H_2O$ bath, for 1 hour. The water was decanted, and the shards were lyophilized.

4.0 M Guanidine HCl/10.0 mM Tris-HCl Extraction. The tooth particles (100 g) were extracted in 250 ml 4.0 M guanidine HCl (GuHCl)/10.0 mM Tris.HCl, plus PIs, pH 7.4 at 4° C. with stirring for 72 hours and daily GuHCl changes. The guanidine extracts were combined and centrifuged at 7000 RPM for 10 min. The soluble supernatant was aliquoted, and the aliquots were stored at −20° C.

Fractionation Procedures

Sephacryl S-100 Chromatography. Aliquots of the GuHCl extract were applied to a 123×2.0 cm internal diameter (ID) Sephacryl S-100 resin (Pharmacia) column. The column was equilibrated and eluted with a degassed 4.0 M GuHCl/10 mM Tris-HCl, pH 7.4 running buffer, at a rate of 35 ml/hour. Optical density was monitored at 226 nm, and fractions were collected at a rate of 10 minutes/tube. Fractions were selected based on the chromatographic profile, dialyzed against $dH_2O$ plus PIs using SpectraPor tubing #3 (MW cutoff of 3,500), lyophilized, and tested in the EMF [$^{35}SO_4$]-incorporation tissue culture assay system.

Gel Electrophoresis. Polyacrylamide-SDS Gel Electrophoresis (PAGE) was carried out according to the method of Laemmli (1970), using 5–15% gradient and 15 or 16 % straight gels. The bCIA proteins were best visualized following SDS-PAGE by a silver staining technique since it has a high sensitivity for the detection of low quantities of protein (Wray et al., 1981).

Reverse PhaseHPLC. Four sequential RP-HPLC steps were used for fractionation of the combined active fractions obtained by the Sephacryl S-100 chromatography; a modification of the procedure of Amar et al. (1991). These last four chromatography steps incorporated varying aqueous trifluoroacetic acid (TFA)/acetonitrile (ACN) gradients, with the first two steps performed on a Vydac (Sep/a/ra/tions Group, Hesperia, Calif.) C18 semi-preparative column (2.2× 25 cm), and the last two steps on a Vydac C18 narrow bore analytical column (0.46×25 cm). Buffer A was 99.9% $dH_2O$; 0.1% TFA, Buffer B was 99.9% ACN; 0.1% TFA. The samples were dissolved in a 90% A, 10% B solution. The samples were applied to the columns and run using varying programs resulting in sequentially more shallow gradient elution of the samples from the columns. The absorbance was monitored at 220 nm. The semi-prep columnm was run at a flow rate of 5 ml/min and the analytical column at a flow rate of 1 ml/min, with 5 ml and 0.5 ml fractions collected, respectively. The resulting HPLC fractions were pooled according to the distribution of peaks on the chromatographic profiles and lyophilized to dryness for activity testing using the EMF $^{35}S$—$SO_4$-incorporation assay.

Characterization of Fractions

Protein Quantitation. The protein fractions were quantitated using the Bio-Rad Protein Assay kit, according to the manufacturers directions.

Amino Acid Composition. Protein fractions were analyzed for their amino acid compositions at the Northwestern University Biotechnology Facility, the Harvard University Microchemistry Facility, or the laboratory of Dr. Frank Barry, Osiris Therapeutics, Baltimore, Md. Samples were lyophilized and then hydrolyzed in 6.0 N HCl at 155° C. for 1 hour.

Amino Acid Sequencing. $NH_2$ amino acid sequencing was performed by the Northwestern University Biotechnology facility. Internal tryptic digestion, and microsequencing was performed at the Harvard Microchemistry Facility, under the direction of Dr. William Lane, or at Osiris Therapeutics. Amino terminal sequencing using automated Edman degradation (Edman, 1950) was performed on an Applied Biosystems (model 477A) sequencer through 20 cycles. The tryptic digestion was performed according to Stone et al. (1989).

Mass Spectral Analysis. Samples were analyzed by Matrix Assisted Laser Desorption Ionization (MALDI) and electrospray (ESI), either at The University of Illinois School of Chemical Sciences mass spectrometry laboratory under the supervision of Dr. Richard Milberg, or at Osiris Therapeutics.

Iodination of Proteins. To better visualize the low quantity of proteins that remained following the extensive fractionation steps, the active fractions from each step were iodinated by the chloramine-T method (McConahey and Dixon, 1966). This entire procedure was performed behind lead shields. To the protein, 750 $\mu$l of 40 mM $NaH_2PO_4$, pH 7.4; 3.3 $\mu$l of $^{125}$I (330 $\mu$Ci); and 100 $\mu$l of 4 mg/ml chloramine-T in 20 mM $NaH_2PO_4$, pH 7.4, were added at room temperature. The contents of the tubes were mixed by tapping, and allowed to react for 30 seconds. The reaction was then neutralized by the addition of 100 $\mu$l of 4 mg/ml sodium metabisulfite. The unincorporated $^{125}$I was removed by separation on a gel filtration column (MW cutoff 1,500) (Pharmacia disposable PD-10 columns prefilled with Sephadex G-15) that had been prewashed with 5 ml of 20 mg BSA/ml PBS, pH 7.4 and 100 ml of PBS minus BSA, pH 7.4. The protein was eluted with PBS, pH 7.4, collecting 1 ml fractions. The incorporation was measured in a gamma counter. The iodinated proteins, which eluted in the 5th and 6th fractions, were pooled, electrophoresed on agarose gels, dried, and exposed to film for visualization.

Figure 2A:
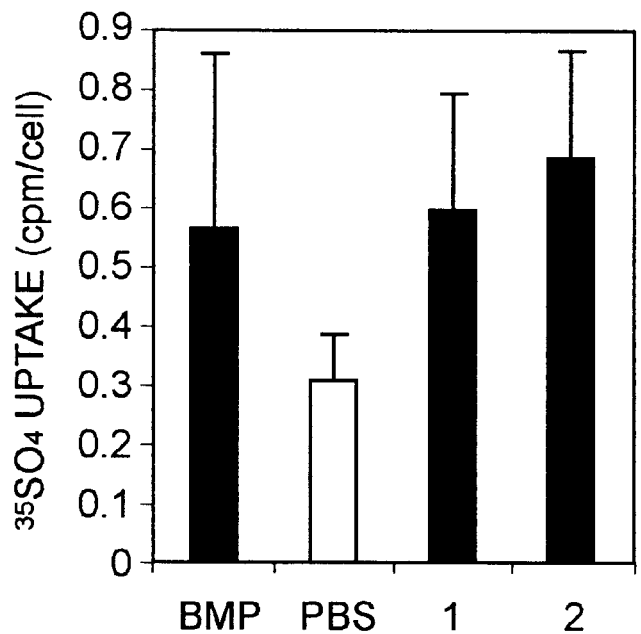
FIG. 2. Assays for the activity of the S-100 fractions in the EMF [$^{35}$S]—SO$_4$-incorporation assay.
Figure 2B:
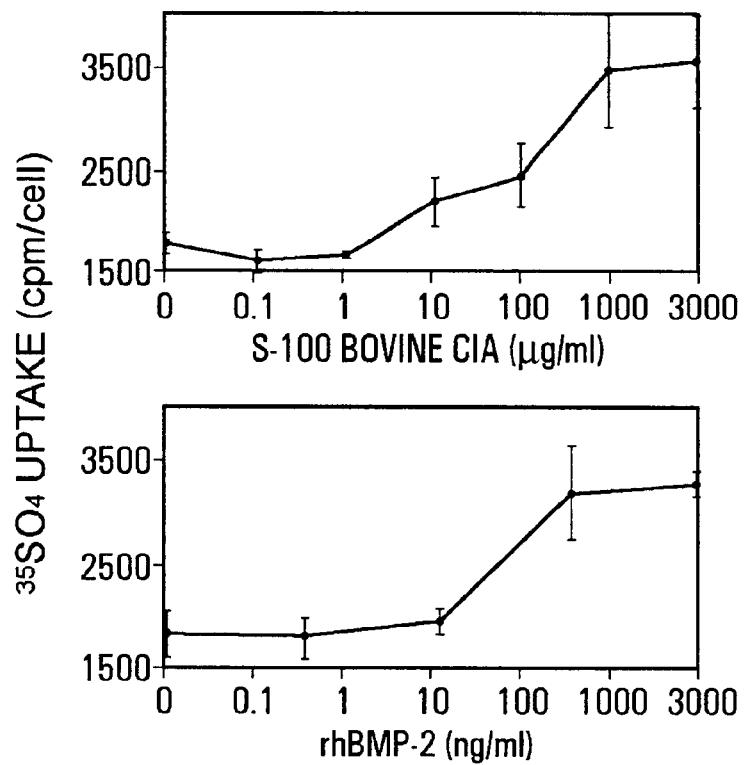

Initial isolation of active crude bCIA. Chromatography on Sephacryl S-100 After all of the steps of the Urist procedure, prior to the final extraction with the 4.0 M GuHCl/10 mM Tris-HCl, approximately 100 g of defatted, demineralized protein was obtained from an initial 780 grams of cleaned mineralized tissue. The total 4.0 M GuHCl/10 mM Tris-HCl extract was approximately 15 g, ~2% of the initial weight. Chromatography on Sephacryl S-100 yielded the optical density profile shown in FIG. 1. The bulk of the protein was in the high molecular mass peak, which was quite compressed and covered a wide range of molecular sizes. However, this set of proteins had no activity. The components of the shoulder beginning at the 17 K $M_r$ marker, labeled fractions 1 and 2, had all of the activity. The sulfate incorporating activities of fractions 1 and 2 were in the same range as the activity of a crude preparation of bovine bone BMP, FIG. 2A, but the concentration required for activity was 1000-fold higher when compared with the activity of rhBMP-2, FIG. 2B.

Gel electrophoresis Gel electrophoresis FIG. 3, confirmed that the majority of the protein in the S-100 fractions 1 and 2 were in the range $M_r$<17 K. Electrophoresis in the absence of reducing agent did not significantly alter the protein profiles. Since the bulk of the components in Fractions 1 and 2 were in the same low molecular weight range, these fractions were combined and denoted as the S-100 fraction, and were used as the starting material for the further purification.

Results

Demonstration that S-100 does stimulate expression of the chondrogenic phenotype.

To verify that the short-term EMF $^{35}SO_4$-incorporation assay was a valid indicator for chondrogenesis, medium term cultures were analyzed for the appearance of message for type II collagen and long term cultures were analyzed for cell morphological changes and the appearance of mineralizing nodules in response to the S-100 fraction. First, the production of type I and type II collagens were followed by Northern analysis. With the rat incisor CIA (Amar et al., 1991) proteins characteristic of cartilage had been detected in EMF cells by day 5 in culture. The EMF cells were therefore grown to near confluence in GM. The medium was then replaced with CM plus 1 mg/ml S-100 (day 0) and culture continued for 6 days. The medium (CM+S-100) was changed at days 2 and 4. The cells were harvested and the mRNA extracted. The mRNA was extracted from a parallel EMF culture at day 0. As shown in the Northern blots in FIG. 4A, the message level for Type I collagen was detected at day 0 following addition of bCIA S-100 fraction into the media of the EMFs. After 6 days in culture the expression of the type I collagen mRNA decreased significantly but was still evident. In contrast, on day 0 no message could be detected for type II collagen, but the type II message was strongly expressed at day 6 (FIG. 4B). Two isoforms of the type II message were evident, at 5.0 and 5.3 kb, at approximately the same intensity.

EMF cultures were exposed to S-100 for culture periods up to 49 days. In this system, one had to use the GM throughout the culture period. The cells were therefore exposed to the S-100 according to the procedure of Iwata et al. (1993). The S-100, in PBS/0.1% BSA was added to uncoated plastic, and then dried and insolubilized by exposure to UV light. T150 plates (150$cm^2$ area) were used. Preliminary studies in 12 well plates were used to determine the optimum amounts of S-100, and bBMP (crude, from Urist) for positive control. In this case, optimal was defined as that amount which permitted long-term viable culture. The optimal amount of S-100 was 100 $\mu g/cm^2$, the bBMP optimum was 200 $\mu g/cm^2$. Those were the amounts used for the final study.

Control cultures, grown on PBS/0.1% BSA, reached confluence in 5 to 7 days and continued as a confluent monolayer of mostly spindle-shaped cells, evenly distributed over the plates through the first two weeks. Over the following two weeks the cell layers lifted off the plates and rolled up. New outgrowths then began to regrow the monolayer. The cells grown on the S-100 and bBMP behaved differently. After reaching confluence in 5–7 days, cells in both culture systems began to increase in density, migrating into cellular accumulations or nodules with overlapping cells. The more elongated cells on the periphery of the nodular areas appeared to be polarized towards the nodule centers. In both cases the nodules stained positively for toluidine blue at 26 days and alizarin red at 49 days in culture (FIG. 5). The cells cultured on PBS/0.1% BSA did not demonstrate any morphological changes or enhanced alcian blue, toluidine blue or alizarin red staining throughout the 49 day period. Thus, the bCIA (S-100) and bBMP behaved differently from the controls in a comparable fashion. There were differences in appearances of the nodules and the intensity of staining, but these were not quantified.

The in vivo implants of rhBMP-2 and S-100 into the Long Evans rats, showed the expected formation of a heavily von Kossa stained mix of cartilage and bone in each implant. The collagen controls showed no evidence of cartilage or bone formation, or of von Kossa staining at the implant sites. The intact dentin matrix implants were heavily mineralized.

All of the above data verified that proteins capable of inducing the chondrogenic phenotype in embryonic muscle fibroblasts in vitro, and in ectopic muscle sites in vivo were present in the S-100 fraction of the bovine dentin extract.

Semi-Preparative Fractionation of the bCIA S-100. The S-100 fraction was dissolved in aqueous 0.1% trifluoroacetic acid (TFA) (A)0.1% TFA in acetonitrile (ACN) (B) solution, at 90% A-10% B, and loaded on a Vydac C18 RP-HPLC semi-prep column. The program consisted of a steep ACN gradient, which changed from 10% to 100% ACN over 35 minutes. The resulting chromatogram yielded a number of distinct peaks, as shown in FIG. 6. Fractions were collected as indicated, and because most of the peaks were quite small, similar fractions from a number of runs (~200 mg S-100/run) were combined. Each fraction was lyophilized to remove the volatile solvents and then tested in the EMF-$^{35}$S—SO$_4$ incorporation assay. The chondrogenic activity was localized to peak #8 (FIG. 6, Inset). It was interesting to note that the major fraction, peak 4 and peak 10 decreased the $^{35}$SO$_4$ incorporation activity well below that of the PBS/BSA control. These fractions may contain inhibitory factors for proteoglycan synthesis.

In comparing their activity, an equal concentration of 57.5 $\mu$g/ml of each fraction was used. Recombinant hBMP-2, at 100 ng/ml and S-100 at 1 mg/ml were used as positive controls. These widely different concentrations suggested that a near 20-fold purification of the bCIA had been achieved in this single step, but that if the bCIA were comparable to the rhBMP-2 in activity, then peak 8 was far from pure. That was also evident in the breadth of peak 8. The appropriate amount of bCIA to use for assay was also a problem. As seen in FIG. 7, peak 8 exhibited a clear-cut inverse concentration dependence of activity in the 1–500 $\mu$g/ml concentration range. At 500 $\mu$g/ml peak 8 activity was not significantly different from the PBS/BSA control. In all subsequent assays, concentration dependence was also determined.

All of peak 8 material was combined from a number of semipreparative runs and then chromatogramed again over a more shallow gradient, but little further separation of peak 8 into sub-components was achieved. Nevertheless, the major component of rechromatogrammed peak 8 (8b) was submitted for Laser Desorption Mass Spectrometry. Peptides with masses 6,797, 10,607, and 22,421 D were prominent, plus smaller amounts of peptides at 14,660 and 29,240 D.

The next step was to use an analytical C-18 reverse phase column with an even more shallow gradient (FIG. 8). Consistent with the mass spectrometry data, Peak 8b was separated into an alarming number of components. Peak 8b-5 contained the activity, but the broad domain labeled as "8b-6" also showed activity. On the supposition that the S-100 might have contained BMP and/or TGF-$\beta$, rhBMP-2 and hTGF-$\beta$1 were chromatogramed using the same program. As shown in the superimposed chromatograms, rhBMP-2 elution corresponded to "6", while TGF-$\beta$1 eluted between "5"and "6".

Further evidence that the protein of 8b-5 was different from TGF-$\beta$1 and BMP was obtained by amino acid analysis. The protein was rich in proline, tyrosine and leucine and contained no detectable cysteine, whereas at least 7 cysteines would have been present per molecule if the bCIA were a member of the BMP family. Acrylamide gel electrophoresis of $^{125}$I-labelled peak 8b-5 yielded a broad band, in the 6,000–10,000 M$_r$ range (FIG. 9) as the major constituent. The mature forms of the BMP family would have had M$_r$ in the range of 14–18 K. Protein of peak 8b-5 was submitted to the microsequencing facility at Osiris Therapeutics, where, under the direction of Dr. Frank Barry, the sample was subjected to trypsin digestion and then sequenced by automated Edman on an Applied Biosystems Procise Sequencer. Four peptides were obtained, two gave the sequences SEQ ID NO:8 and SEQ ID NO:9; the other two yielded the sequence SEQ ID NO:7. A search of the Swiss-Protein peptide sequence data bases showed that the two sequences generated corresponded 100 % with the sequence of bovine amelogenin. SEQ ID NO:7 is the amino-terminal sequence of the mature, secreted protein, SEQ ID NO:9 follows the first internal lysine residue.

The components of fraction 8b-5 showed sulfate incorporation activity in the range from 50 ng/ml to 1 $\mu$g/ml concentrations, approaching the range of specific activity of rhBMP-2.

Bovine molar teeth, in common with the teeth of other herbivores, have very complex structures in which the enamel is enfolded into the dentin. They also contain clefts that contain coronal cementum. Even when frozen in liquid N$_2$ and shattered, it is impossible to separate these components mechanically among the shards. Thus, the crushed, demineralized bovine tooth matrix might contain proteins from all of these sources. Rat incisors have enamel on the labial side of the tooth and cementum on the lingual side. Since it is virtually impossible to remove all of these mineralized tissues prior to preparing dentin extracts, the extracts will always exhibit some degree of contamination. Usually the amount of mineralized dentin far exceeds the amount of cementum, and since the protein content of the enamel is so low, one can generally assume that the major protein components of a dentin extract originated in the dentin. This may not be the case in the present instance, where the proteins of interest appear to be present and active at the cytokine level. The behavior of the S-100 fractions of the rat incisor (Amar et al., 1991) and bovine dentin extracts were comparable, however, in spite of the markedly enhanced ease of cleaning the rat incisors. Thus, we have retained language suggesting that the bCIA is a dentin component.

The S-100 fraction of the bovine dentin extract was a mixture of a number of low M$_r$ proteins (FIG. 3). In culture, this fraction promoted enhanced sulfate incorporation into proteoglycans (FIG. 2) and led to morphological changes in the appearance of embryonic muscle fibroblasts with the development of an acidic proteoglycan-rich extracellular matrix (FIG. 5), and the expression of the mRNA for type II collagen and down regulation of type I collagen mRNA (FIG. 4). These changes in cell phenotype were seen within the period from day 1 to day 6 in culture. On long term culture (49 days), multilayered nodules rich in proteoglycan (Toluidine Blue stained) were formed. Alizarin Red staining showed the presence of mineralization within these nodules even without the addition of $\beta$-glycerol phosphate to the cultures (FIG. 5). Implants of the S-100 fraction in vivo in muscle pouches, also led to bone-like matrix development based on a chondrogenic model of the implant within a nine week period. The correlations between these data confirmed the short term sulfate incorporation assay as a valid system for the assessment of the bioactivity of the chondrogenic/osteogenic inducing agents in dentin.

Example 2

Cloning and Sequencing of Amelogenin Peptides

Freshly extracted rat incisors were cleaned to remove the soft enamel. The odontoblasts and pulp cells were retained. Poly A+ RNA was isolated from these cells using the Oligotex mRNA kit (Qiagen). The mRNA was converted to first strand cDNA using an 18mer oligo(dT) and superscript II reverse transcriptase (Life Technologies). The first strand cDNA was subsequently used in a PCR reaction. The forward primer P1, SEQ ID NO:10, was based on the amelogenin amino terminal peptide sequence SEQ ID NO:7 and the reverse primer P2 SEQ ID NO:11 corresponded to the tryptic peptide sequence SEQ ID NO:8. The PCR conditions were 95° C. for 1 min., 55° C. for 1 min., and 72° C. for 1 min. for 25 cycles. The PCR amplified bands were cloned in pGEMT vector and sequenced. Each of the amplified bands was used to screen the λgt 11 cDNA library prepared from rat incisor odontoblasts as described by George et al. (1993). Positive clones were picked and plaque purified through three successive rounds of screening. A single pure plaque was then amplified and the phage DNA was prepared according to established procedures (Maniatis et al., 1989). The phage DNA was digested with EcoRI, cloned into the EcoRI site of pbluescript KS and sequenced.

In order to place the sequenced peptides in their full-length amelogenin sequence contexts, two new primers were designed. Forward primer P3 SEQ ID NO:12 contained a unique EcoRI site and included the ATG start codon and first fifteen nucleotides. The reverse primer P4 SEQ ID NO:13 contained a unique XhoI site and included the last 15 nucleotides and the stop codon TAA. These primers were used in a PCR reaction using the phage DNA obtained from amplification of the entire odontoblast library as template, with the PCR conditions as described above. The PCR amplified bands were cloned in pGEMT vector and sequenced.

Expression of the Cloned Amelogenins. The cloned amelogenins were expressed as GST-fusion proteins. The inserts in pGEMT were re-amplified by PCR, using the primers P3 and P4 and conditions described above. The PCR products were digested with EcoRI and xhoI, purified on a 1% agarose gel and cloned in frame into the EcoRI/XboI site of the GST expression vector pGEXT4. The resulting plasmid was introduced into the *E. coli* strain BL21 (DE3). For preparation of the fusion protein, a single colony was inoculated into 10 ml of LB and grown overnight. An additional 990 ml of LB was added and growth continued for 4 h, after which IPTG was added to a final concentration of 1 μM. Incubation was carried on for an additional 4 h. The expressed protein was then passed over and collected on a Glutathione-Sepharose affinity column (Pharmacia) according to the manufacturer's instructions. For different purposes the fusion proteins were either directly eluted from the column with excess glutathione or the bound protein was treated with thrombin to release the recombinant peptide.

Isolation of Peptides. In most preparations, the thrombin released peptides were a heterogeneous mixture, containing some prematurely terminated peptides as well as full-length peptide. Therefore the thrombin cleaved, eluted protein was passed over a C-18 reverse phase column eluted by an increasing gradient of acetonitrile plus 1% trifluoroacetic acid as described in Example 1. for the final step of purification of the protein extracted from dentin matrix.

Assays for Biological Activity

In vitro assay for chondrogenic activity: The purified recombinant proteins were tested for biological activity by the assay for enhanced incorporation of $^{35}S$—$SO_4$ into proteoglycan (8,11) by embryonic rat muscle fibroblasts (EMF). The EMF were seeded onto type I collagen coated 96 well plates, with an initial loading of $10^4$ cell/well. The cells were grown to near confluence in alpha MEM, 10% FBS, 1% Pen/Strep in 5 days. At day 5 the growth media was replaced with conditioning media (CM), alpha MEM, 0.5% FBS, 1% Pen/Strep, and grown for an additional 24 h. Fresh CM containing the factors to be tested, was added at the concentrations noted. Four hours later, $1\,\mu Ci^{35}S$—$SO_4$ in 10 μL sterile PBS was added per well, and incubation was continued for 20 h. The $^{35}S$—$SO_4$ incorporated into secreted proteoglycan was determined by precipitation of the proteoglycan with cetyl pyridinium chloride, as described above, followed by scintillation counting of the precipitate. The cell layer was trypsinized and the number of cells counted. Incorporation is presented as counts per minute per cell $\times 10^3$. Recombinant human BMP2 (A kind gift from the Genetics Institute, Boston, Mass.) and the bioactive crude S100 fractions from rat incisor dentin (Amar et al., 1991) and/or bovine dentin (see Example 1) were used as the positive controls. Bovine serum albumin in phosphate buffered saline (PBS) was the negative control. A commercial preparation of purified porcine amelogenins, known as Emdogain (Biora AB, Malmö, Sweden) (Hammarström, 1997) was also tested.

In vivo osteogenic activity. The recombinant proteins, Emdogain and controls were each included in a bioabsorbable polymer matrix implants. The implants were prepared in poly (lactide)-poly(glycolide) scaffolds by the procedure of Whang et al. (1998) with 167 μg per implant. Implants were placed in the quadriceps of the hind legs of 100 g, 4 week old, male Long-Evans rats. Each animal received a negative control implant containing 167 μg of BSA in PBS. The implants were kept in place for 28 days. The implants were removed and radiographed, then they were fixed in 4% paraformaldehyde, dehydrated in graded ethanol and embedded in paraffin. Sections (7μ thick) were cut and stained with either Von Kossa or Alizarin Red dyes, both of which can indicate the presence of mineralized deposits containing divalent cations. To assure that the stains seen were calcific deposits, serial sections were treated with 5% EGTA for 10 min before staining.

Results

Cloning and Sequencing Two PCR products were detected, corresponding to the amino acid sequences, PCR1 SEQ ID NO:14, and PCR2 SEQ ID NO:15. PCR1 was much more intense than PCR2, and corresponded to the expected complete amino terminal sequence from amelogenin gene exons 2, 3 and 5. Unexpectedly, PCR2 included exon 4. The presence of protein containing the 14 amino acid sequence corresponding to exon 4 in the rat has not been previously reported. These data established that differentially spliced amelogenin mRNAs containing exons 2, 3, 4 and 5 and exons 2, 3 and 5 for both sequenced peptides were indeed present when the CDNA library was constructed. Based on the higher intensity of PCR1 on the gels it is likely that there was a higher concentration of its mRNA than for the transcript containing exon 4, in PCR2.

PCR1 and PCR2 would be expected to be present in all of the usual amelogenin gene splice products. To determine the full-length sequences of the amelogenin mRNA coding regions present in the odontoblast cDNA library, new PCR primers P3 and P4 were prepared. Four PCR product bands were amplified from the template phage DNA, at approximate sizes 650, 600, 250 and 200 bp. PCR600 and PCR200 were strong, PCR650 and PCR250 were weak. All four bands were amplified, FIG. 10, and cloned in pGEMT vector and sequenced. These data showed that mRNAs for four specific amnelogenin gene splice products had been present when the rat incisor odontoblast-pulp cDNA library was created: PCR650, SEQ ID NO:16 corresponding to exons 2, 3, 4, 5, 6 and 7; PCR600, SEQ ID NO:17 corresponding to exons 2, 3, 5, 6 and 7; PCR250 SEQ ID NO:6 corresponding to exons 2, 3, 4, 5, 6d and 7; and PCR200 SEQ ID NO:5 corresponding to exons 2, 3, 5, 6d and 7,. The nucleotide and amino acid sequences for PCR250, which is rA4, are shown in FIG. 11B. The splice patterns for the four PCR products are also shown.

Gel electrophoresis showed the cloned and expressed amelogenin fusion proteins, collected from a Glutathione-Sepharose affinity column, to be rich in the desired full-length polypeptides, but some lower mass, incompletely elongated peptides were present, along with other protein impurities. The eluted proteins were therefore fractionated by reverse phase HPLC using the same system as the final step in the isolation of the purified polypeptides from the tissue described in Example 1, yielding the pure peptides, as shown in FIG. 12 for r(A-4) (PCR200).

In vitro $^{35}$S—SO$_4$ incorporation assay. The data in FIG. 13 showed that r(A-4) was active in stimulating production of $^{35}$S—SO$_4$-labeled proteoglycan by embryonic rat muscle fibroblasts in monolayer culture, at a concentration as low as 1 ng/ml, ~140 pM. The rA4 was less active at equivalent concentrations, but was quite comparable to the effect of rhBMP-2 used as a positive control at 10 ng/ml. In vitro the r(A-4) did not act as a growth factor. Even after 5 days in culture, after a 24 h exposure to r(A-4), the cell number did not increase as it did in the presence of rhBMP2 and rA4. While similar, the effects of r(A-4) and rA4 were distinguishable. The commercial preparation of porcine amelogenins known as Emdogain was not effective in this assay at such low concentrations but activity was seen at concentrations greater than 500 μg/ml.

In vivo implant assay The results are shown in FIG. 14. After 4 weeks, implants with r(A-4) stained strongly with Alizarin Red and von Kossa, showing the presence of mineral deposits. The in vivo assay distinguished between rA4 and r(A-4). The rA4 implants were calcified to a lesser extent, with restricted, more focal deposits, but clearly more strongly mineralized than the BSA negative control. Treatment of the rA4 and r(A-4) sections with EGTA eliminated the Alizarin Red and von Kossa staining in the implants (FIG. 14, micrographs 3 & 6), verifying that the X-ray opaque areas seen in panel 9, FIG. 14, represented calcium phosphate deposits in the implants. The r(A-4) implants were also shown to be positive for alkaline phosphatase, another marker of mineralizing systems. Recombinant full-length amelogenins, rB4 and r(B-4) were inactive. The r(A-4) and rA4 implants had become vascularized and filled with extracellular matrix within 4 weeks, FIG. 15. The ingrowth of capillaries was more prominent in the r(A-4) implants, as was the formation of the extracellular matrix. However, islands of capillaries, and the formation of a surrounding extracellular matrix was also evident in the rA4 implants.

Certain small splice products of the amelogenin gene are present in trace amounts in dentin. The presence of the gene product was determined on the basis of a fractionation scheme focused on bioacfivity.

We have traced the ability of amelogenin polypeptides to induce embryonic fibroblastic mesenchymal cells to alter their phenotypic expression and exhibit, in culture, a chondrogenic phenotype. In the more complex in vivo implants in muscle, where other systemic cytokines and inductive factors are present to modulate the interactions, chondrogenesis proceeds to osteogenesis.

Cited Literature

Amar S, Sires B, Sabsay B, Clohisy J, Veis A. (1991) The isolation and partial characterization of a rat incisor dentin matrix polypeptide with in vitro chondrogenic activity. *J Biol Chem* 266: 8609–8618.

Bang G, Urist M R. (1967) Bone induction in excavation chambers of decalcified dentin. *Arch Surg* 94:781–789.

Bessho K, Tagawa T, Murata M. (1990) Purification of rabbit bone morphogenetic protein derived from bone, dentin and wound tissue after extraction. *J Oral Maxillofac Surg* 48:162–169.

Bessho K, Tanaka T, Matsumoto J, Tagawa T, Murata M. (1991) Human dentin matrix-derived bone morphogenetic protein. *J Dent Res* 70:171–175.

Bonass W A, Robinson P A, Kirkham J, Shore R C, Robinson C 1994 Molecular cloning and DNA sequence analysis of mammalian amelogenin protein sequence divergence. Biochem Biophys Res Commun 198:755–763.

Deutsch D, Catalano-Shernan J, Dafni L, David S, Palmon A. (1995) Enamel matrix proteins and ameloblast biology. *Connect Tissue Res* 32: 97–107.

Edman P. (1950) Method for determination of the amino acid sequence in peptides. *Acta Chemica Scand* 4:283–293.

Fincham A G, Moradian-Oldak J. (1995) Recent advances in amelogenin biochemistry. *Connect Tissue Res* 32: 119–124.

George A, Sabsay B, Simonian P A, Veis A 1993 Characterization of a novel dentin matrix acidic phosphoprotein. Implications for induction of biomineralization . J Biol Chem 268: 12624–12630.

George A, Silberstein R, Veis, A. (1995) In situ hybridization shows Dmpl (AG1) to be a developmentally regulated dentin-specific protein produced by mature odontoblasts. *Connect Tissue Res* 33: 67–72.

Gibson C W, Golub E E, Abrams W R, Shen G, Ding W, Rosenbloom J.(1992) Bovine Amelogenin Message Heterogeneity: Alternative Splicing and Y-Chromosomal Gene Transcription. *Biochemistry* 31 :8384–8388.

Gibson C W, Kucich U, Collier P, Shen G, Decker S, Bashir M, Rosenbloom J. (1995) Analysis of amelogenin proteins using monospecific antibodies to defined sequences. *Connect Tissue Res* 32: 109–114.

Hammarström L. (1997) Enamel matrix, cementum development and regeneration. *J Clin Periodontal* 24:658–668.

Hammarström L, Heijl L, Gestrelius S. (1997) Periodontal regeneration in a buccal dehiscence model of monkeys after application of enamel matrix proteins. *J Clin Periodontol* 24:669–677.

Iwata H, Satomi O, Sato K Sato T, Kawamura M. (1993) Bone morphogenetic protein-induced muscle and synovium-derived cartilage differentiation in vitro. *J Dent Res* 65:12–22.

Kohno K, Martin G R, Yamada Y. (1984) Isolation and characterization of a DNA clone for the amino-terminal portion of the pro-α1(II) chain of cartilage collagen. *J Biol Chem* 259: 13668–13673.

Koskinen K P, Kanwar Y S, Sires B, Veis A. (1985) An electron microscopic demonstration of induction of chondrogenesis in neonatal rat muscle outgrowth cells in monolayer cultures. *Connect Tissue Res* 14: 141–158.

Kulkarni G V, Jee M, Thotakura S, Marks S Jr, Veis A, George A (1998) Comparative expression of DMPs and procollagen in normal and osteoporotic mice. *J Dent Res* 77 (Abstr): 723.

Laemmli U K. (1970) Cleavage of structural proteins during the assembly of the head of bacteriophage T4. *Nature* 227:680–685.

Lumsden A G S (1988) Spatial organization of the epithelium and the role of the neural crest cells in the initiation of the mammalian tooth germ. *Development Suppl* 103:155–169.

Lyons K M, Pelton R W, Hogan B L. (1990) Organogenesis and pattern formation in the mouse: RNA distribution patterns suggest a role for bone morphogenetic protein BMP-2A. *Development* 109:833–844.

MacDougall M, Gu T T, Luan X, Simmons D, Chen J. (1998) Identification of a novel isoform of mouse dentin matrix protein 1: spatial expression in mineralized tissues. *J Bone Mineral Res* 13:422–431.

Maniatis T, Fritch E F, Sambrook J 1989 Molecular Cloning: A Laboratory Manual, $2^{th}$ Edition, Cold Spring Harbor, N.Y.

McConahey P J, Dixon F J. (1966) A method of trace iodination of proteins for immunologic studies. *Int Arch Allergy* 29:185–189.

Salido E C, Yen P H, Koprivnikar K, Yu L C, Shapiro, L J. (1992) The Human Enamel Protein Gene Amelogenin Is Expressed from Both the X and Y Chromosomes. *Am.J.Hum.Genet.* 50:303–316.

Sawada T, Nanci A. (1995) Spatial distribution of enamel proteins and fibronectin at early stages of rat incisor tooth formation. *Arch Oral Biol* 40: 1029–1038.

Simmer J P 1995 Alternative splicing of amelogenins. Connective Tissue Res, 1995 32:131–136.

Slavkin H C, Boyde A. (1975) Cementum: An epithelial secretory product? *J Dent Res* 53:157 (Abstr. 409).

Slavkin H C, Bringas J R P, Snead M, Zeichner-David M. (1989) Human and mouse cementum proteins are immunologically related to enamel proteins. *Biochem Biophys Acta* 991: 12–18.

Somerman M J, Nathanson M A, Sauk J J, Manson B. (1987) Human dentin matrix induces cartilage formation in vitro by mesenchymal derived from embryonic muscle. *J Dent Res* 66:1551–1558.

Stone K L, LoPresti M B, Crawford J M, DeAngelis R, Williams K R. (1989) Enzymatic digestion of proteins and HPLC peptide isolation. In: A practical guide to protein and peptide purification. Matsudaira P T, editor. San Diego, Academic Press, pp 37–39.

Urist M R. (1965) Bone: Formation by autoinduction. *Science* 150: 893–899.

Urist M R, Chang J, Lietze A, Huo Y K, Brownell A G, DeLange R J. (1987) Purification and bioassay of bone morphogenetic protein and polypeptide fragments. *Methods Enzymol* 146: 294–312.

Urist M R, Strates B S. (1971) Bone morphogenetic protein. *J Dent Res* (Suppl 6) 50:1392–1406.

Vainio S, Karavanova I, Jowett A, Thesleff I. (1993) Identification of BMP-4 as a signal mediating secondary induction between epithelial and mesenchymal tissues during early tooth development. *Cell* 75:4514 58.

Veis A, Sires B, Clohisy J. (1989) A search for the osteogenic factors in dentin. Rat incisor dentin contains a factor stimulating rat muscle cells in vitro to incorporate sulfate into an altered proteoglycan. *Connect Tissue Res* 23: 135–144.

Veis A, Sires B, Clohisy J, Sabsay B, Amar S 1990 Rat incisor dentine contains a factor which alters the phenotypic expression and stimulates chondrogenesis in fibroblast-like cells in vitro Biomaterials 1135–37.

Wang E A, Rosen V, Cordes P, Hewick R M, Kriz M J, Luxenberg D P, Sibley B S, Wozney J M. (1988) Purification and characterization of other distinct bone-inducing factors. *Proc Natl Acad Sci USA* 85:9484–9488.

Whang K, Tsai D C, Nam E K, Aitken M, Sprague S M, Patel P K, Healy K E 1998 Ectopic bone formation via rhBMP-2 delivery from porous bioabsorbable polymer scaffolds. J Biomed Materials Res 42:491–499.

Wozney J M, Rosen V, Celeste A J, Mitsock L M, Whitters M J, Kriz R W, Hewick R M, Wang E A. (1988) Novel regulators of bone formation: molecular clones and activities. *Science* 242: 1528–1534.

Wray W, Boulikas T, Wray V P. (1981) Silver staining of proteins in polyacrylamide gels. *Anal Biochem* 118:197–203.

What is claimed is:

1. A method for enhancing the generation of bone comprising administering to a manunal a composition comprising a chondrogenic/osteogenic inducing molecule in an amount effective to enhance the generation of bone, said composition comprising a protein having the sequence set forth in SEQ ID NO:5 or a protein having a sequence that has at least 70% homology with the sequence of SEQ ID NO:5 and is capable of inducing chondrogenesis.

2. The method of claim 1, wherein said chondrogenic/osteogenic inducing molecule is a variant of SEQ ID NO:5 that has at least 90% homology with the sequence set forth in SEQ ID NO:5 and is capable of inducing chondrogenesis.

3. The method of claim 1, wherein said chondrogenic/osteogenic inducing molecule is a variant of SEQ ID NO:5 that has a sequence that has at least 95% homology with the sequence set forth in SEQ ID NO:5 and is capable of inducing chondrogenesis.

4. The method of any of claims 1, 2, or 3, wherein said variant of the sequence set forth in SEQ ID NO:5 stimulates proteoglycan production in the mammalian muscle fibroblasts.

5. The method of claim 1, wherein said chondrogenic/osteogenic inducing molecule is administered to said mammal imbedded in a biologically compatible implant matrix at an ectopic site in said mammal.

6. The method of claim 1, wherein said biologically compatible implant matrix is vascularized by tissue surrounded the implantation site.

7. A method for enhancing the generation of bone comprising administering to a mammal a chondrogenic/osteogenic inducing molecule in an amount effective to enhance the generation of bone, wherein said chondrogenic/osteogenic inducing molecule is encoded by a nucleic acid molecule having the nucleotide sequence set forth in SEQ ID NO:2.

8. A method for enhancing the generation of bone comprising administering to a mammal a chondrogenic/osteogenic inducing molecule in an amount effective to enhance the generation of bone, wherein said chondrogenic/osteogenic inducing molecule has the amino acid sequence set forth in SEQ ID NO:5.

9. The method of any of claims 1, 7, 8, 2, or 3, wherein said administration comprises contacting said chondrogenic/osteogenic inducing molecule in an ectopic muscle site in said mammal.

10. The method of claim 9, wherein said contacting produces cartilage at the site of said contacting.

11. The method of claim 9, wherein said contacting produces calcification at the site of said contacting.

* * * * *

UNITED STATES PATENT AND TRADEMARK OFFICE
CERTIFICATE OF CORRECTION

PATENT NO. : 6,677,306 B1
DATED : January 13, 2004
INVENTOR(S) : Arthur Veis et al.

It is certified that error appears in the above-identified patent and that said Letters Patent is hereby corrected as shown below:

<u>Title page,</u>
Item [75], Inventors, "Houston, TX (US)" should be -- Pearland, TX (US) --

<u>Column 37,</u>
Line 3, "manunal" should be -- mammal --
Line 7, "SEQ ID NO:5" should be -- SEQ ID NO:5, --

<u>Column 38,</u>
Line 17, "claims 1, 7, 8, 2, or 3" should be -- claims 1, 2, 3, 7 or 8, --

Signed and Sealed this

Eighth Day of June, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,677,306 B1  
DATED : January 13, 2004  
INVENTOR(S) : Arthur Veis et al.

It is certified that error appears in the above-identified patent and that said Letters Patent is hereby corrected as shown below:

Title page,
Item [75], Inventors, "Houston, TX (US)" should be -- Pearland, TX (US) --

Column 37,
Line 3, "manunal" should be -- mammal --
Line 7, "SEQ ID NO:5" should be -- SEQ ID NO:5, --

Column 38,
Line 17, "claims 1, 7, 8, 2, or 3" should be -- claims 1, 2, 3, 7 or 8, --

Signed and Sealed this

Twenty-second Day of June, 2004

JON W. DUDAS
*Acting Director of the United States Patent and Trademark Office*